(12) United States Patent  (10) Patent No.: US 7,883,031 B2
Collins, Jr. et al.  (45) Date of Patent: Feb. 8, 2011

(54) OPHTHALMIC DRUG DELIVERY SYSTEM

(75) Inventors: James F. Collins, Jr., 2-01 50th Ave., Apt 3R, Long Island City, NY (US) 11101; Randal B. Chinnock, Sturbridge, MA (US); Jeffrey Melanson, Sturbridge, MA (US); Joseph Howard, Bayshore, NY (US)

(73) Assignee: James F. Collins, Jr., Long Island City, NY (US)

( * ) Notice: Subject to any disclaimer, the term of this patent is extended or adjusted under 35 U.S.C. 154(b) by 132 days.

(21) Appl. No.: 10/851,611

(22) Filed: May 20, 2004

(65) Prior Publication Data

US 2004/0256487 A1   Dec. 23, 2004

Related U.S. Application Data

(60) Provisional application No. 60/471,883, filed on May 20, 2003, provisional application No. 60/485,305, filed on Jul. 3, 2003.

(51) Int. Cl.
*A61M 11/06* (2006.01)
(52) U.S. Cl. ............ 239/338; 239/102.2; 239/375; 239/360; 128/200.14; 128/200.16
(58) Field of Classification Search ... 239/102.1–102.2, 239/375, 378, 338, 329, 330, 71, 74, 360; 222/64, 66, 639, 642; 310/327, 326; 251/129.06; 128/200.14, 200.16
See application file for complete search history.

(56) References Cited

U.S. PATENT DOCUMENTS

| 429,407 | A | * | 6/1890 | Reichl et al ............... 295/15 |
|---|---|---|---|---|
| D772,028 | | | 10/1904 | Carpenter |
| 1,482,747 | A | | 2/1924 | Howe |
| 1,988,637 | A | | 1/1935 | Tinkham |
| 2,189,643 | A | | 2/1940 | Ward |
| 2,200,008 | A | | 5/1940 | Nowak |
| 2,249,608 | A | | 7/1941 | Greene |

(Continued)

FOREIGN PATENT DOCUMENTS

DE   199 34 582   1/2001

(Continued)

OTHER PUBLICATIONS

International Search Report, mailed Sep. 2, 2004.

(Continued)

*Primary Examiner*—Len Tran
*Assistant Examiner*—Jason J Boeckmann
(74) *Attorney, Agent, or Firm*—Brinks Hofer Gilson & Lione

(57) ABSTRACT

A fluid atomizer is disclosed. The fluid atomizer comprises a body having a proximal end and a distal end. A removable reservoir containing a fluid disposed therein is connected to the body. A discharge plate is disposed at the distal end, wherein the discharge plate includes a plurality of openings extending therethrough. An ultrasonic oscillator is disposed in the body for transmitting the fluid from the reservoir to the discharge plate and through the plurality of openings, wherein transmission of the fluid through the plurality of openings atomizes the fluid.

70 Claims, 22 Drawing Sheets

U.S. PATENT DOCUMENTS

| | | |
|---|---|---|
| 2,552,857 A | 5/1951 | Knapp |
| 2,595,317 A | 5/1952 | White, Jr. |
| 2,987,439 A | 6/1961 | Wittlinger |
| 3,170,462 A | 2/1965 | Hall |
| 3,237,809 A | 3/1966 | Daragan et al. |
| 3,310,830 A | 3/1967 | Gattone |
| 3,314,426 A | 4/1967 | Carroll |
| 3,439,674 A | 4/1969 | Lelicoff |
| 3,602,399 A | 8/1971 | Litman et al. |
| 3,658,257 A | 4/1972 | Rood |
| 3,779,245 A | 12/1973 | Windsor |
| 3,780,950 A | 12/1973 | Brennan |
| 3,795,351 A | 3/1974 | Lehmann |
| 3,812,854 A | 5/1974 | Michaels et al. |
| 3,826,258 A | 7/1974 | Abraham |
| 3,845,764 A | 11/1974 | Windsor |
| 3,901,443 A | 8/1975 | Mitsui et al. |
| 3,906,949 A | 9/1975 | Holland |
| 3,913,575 A | 10/1975 | Windsor |
| 3,934,585 A | 1/1976 | Maurice |
| 4,002,168 A | 1/1977 | Petterson |
| 4,052,985 A | 10/1977 | Coleman et al. |
| 4,067,499 A | 1/1978 | Cohen |
| D249,709 S | 9/1978 | Trovinger |
| 4,119,096 A | 10/1978 | Drews |
| 4,122,556 A | 10/1978 | Poler |
| 4,131,115 A | 12/1978 | Peng |
| 4,173,226 A | 11/1979 | Shell |
| 4,175,704 A | 11/1979 | Cohen |
| 4,175,706 A | 11/1979 | Gerstmann |
| 4,264,837 A | 4/1981 | Gaboriaud |
| 4,296,071 A | 10/1981 | Weiss et al. |
| 4,319,155 A | 3/1982 | Nakai et al. |
| 4,323,530 A | 4/1982 | Voss et al. |
| 4,338,936 A | 7/1982 | Nelson |
| 4,356,528 A | 10/1982 | Coffee |
| 4,381,533 A | 4/1983 | Coffee |
| 4,390,542 A | 6/1983 | Schachar |
| 4,398,909 A | 8/1983 | Portnoff |
| 4,465,234 A | 8/1984 | Maehara et al. |
| 4,471,890 A | 9/1984 | Dougherty |
| 4,476,515 A | 10/1984 | Coffee |
| 4,479,609 A | 10/1984 | Maeda et al. |
| 4,493,119 A | 1/1985 | Baumann |
| 4,543,096 A | 9/1985 | Keene |
| 4,544,570 A | 10/1985 | Plunkett et al. |
| 4,564,016 A | 1/1986 | Maurice et al. |
| 4,580,721 A * | 4/1986 | Coffee et al. ................... 239/3 |
| 4,605,167 A | 8/1986 | Maehara |
| 4,605,398 A | 8/1986 | Herrick |
| 4,627,845 A | 12/1986 | DeMotte |
| 4,641,384 A | 2/1987 | Landsberger et al. |
| 4,642,581 A | 2/1987 | Erickson |
| 4,658,290 A | 4/1987 | McKenna |
| 4,659,014 A | 4/1987 | Soth et al. |
| 4,679,551 A | 7/1987 | Anthony |
| 4,685,906 A | 8/1987 | Murphy |
| 4,701,167 A | 10/1987 | Chekan |
| 4,702,418 A | 10/1987 | Carter et al. |
| 4,706,848 A | 11/1987 | D'Andrade |
| 4,740,206 A | 4/1988 | Allander |
| 4,742,713 A | 5/1988 | Abe et al. |
| 4,750,650 A | 6/1988 | Ling |
| 4,750,902 A | 6/1988 | Wuchinich et al. |
| 4,758,237 A | 7/1988 | Sacks |
| 4,758,727 A | 7/1988 | Tomei et al. |
| 4,759,755 A | 7/1988 | Hein et al. |
| 4,779,768 A | 10/1988 | St. Amand |
| 4,784,652 A | 11/1988 | Wikstrom |
| 4,790,479 A | 12/1988 | Matsumoto et al. |
| 4,792,334 A | 12/1988 | Py |
| 4,793,339 A | 12/1988 | Matsumoto et al. |
| 4,796,807 A | 1/1989 | Bendig et al. |
| 4,798,599 A | 1/1989 | Thomas |
| 4,809,914 A | 3/1989 | Goncalves |
| 4,815,661 A | 3/1989 | Anthony |
| 4,826,025 A | 5/1989 | Abiko et al. |
| 4,850,534 A | 7/1989 | Takahashi et al. |
| 4,863,073 A | 9/1989 | Burt et al. |
| 4,863,443 A | 9/1989 | Hornung |
| 4,863,457 A | 9/1989 | Lee |
| 4,871,091 A | 10/1989 | Preziosi |
| 4,877,989 A | 10/1989 | Drews et al. |
| 4,880,146 A | 11/1989 | Hudgins |
| 4,886,189 A | 12/1989 | Vanderjagt |
| 4,896,832 A | 1/1990 | Howlett |
| 4,908,024 A | 3/1990 | Py |
| 4,912,357 A | 3/1990 | Drews et al. |
| 4,917,274 A | 4/1990 | Asa et al. |
| 4,927,062 A | 5/1990 | Walsh |
| 4,927,115 A | 5/1990 | Bahroos et al. |
| 4,946,452 A | 8/1990 | Py |
| 4,952,212 A * | 8/1990 | Booth et al. ................. 604/294 |
| 4,961,885 A | 10/1990 | Avrahami et al. |
| 4,969,869 A | 11/1990 | Burgin et al. |
| 4,981,479 A | 1/1991 | Py |
| 4,996,502 A | 2/1991 | Endo |
| 5,007,905 A | 4/1991 | Bauer |
| 5,019,037 A | 5/1991 | Wang et al. |
| 5,029,579 A | 7/1991 | Trammell |
| 5,030,214 A | 7/1991 | Spector |
| 5,032,111 A | 7/1991 | Morris et al. |
| 5,037,012 A | 8/1991 | Langford |
| 5,040,706 A | 8/1991 | Davis et al. |
| 5,047,009 A | 9/1991 | Morris et al. |
| 5,048,727 A | 9/1991 | Vlasich |
| 5,053,000 A | 10/1991 | Booth et al. |
| 5,054,477 A | 10/1991 | Terada et al. |
| 5,064,420 A | 11/1991 | Clarke et al. |
| 5,066,276 A | 11/1991 | Wang |
| 5,069,675 A | 12/1991 | Menchel et al. |
| 5,085,651 A | 2/1992 | Py |
| 5,098,375 A | 3/1992 | Baier |
| 5,133,702 A | 7/1992 | Py |
| 5,134,993 A | 8/1992 | Van der Linden et al. |
| 5,139,496 A | 8/1992 | Hed |
| 5,145,113 A | 9/1992 | Burwell et al. |
| 5,152,435 A | 10/1992 | Stand et al. |
| 5,152,456 A * | 10/1992 | Ross et al. ................. 239/102.2 |
| 5,163,929 A | 11/1992 | Py |
| 5,164,740 A | 11/1992 | Ivri |
| 5,170,782 A | 12/1992 | Kocinski |
| 5,176,856 A | 1/1993 | Takahashi et al. |
| 5,193,745 A | 3/1993 | Holm |
| 5,201,726 A | 4/1993 | Kirkham |
| 5,203,506 A | 4/1993 | Gross et al. |
| 5,226,538 A * | 7/1993 | Roselle .................... 206/459.1 |
| 5,259,385 A | 11/1993 | Miller et al. |
| 5,261,601 A | 11/1993 | Ross et al. |
| 5,267,986 A | 12/1993 | Py |
| 5,276,867 A | 1/1994 | Kenley et al. |
| 5,299,739 A | 4/1994 | Takahashi et al. |
| 5,318,014 A | 6/1994 | Carter |
| 5,320,845 A | 6/1994 | Py |
| 5,354,032 A | 10/1994 | Sims et al. |
| 5,364,405 A | 11/1994 | Zaleski |
| 5,368,582 A | 11/1994 | Bertera |
| 5,401,259 A | 3/1995 | Py |
| 5,405,614 A | 4/1995 | D'Angelo et al. |
| 5,431,663 A | 7/1995 | Carter |
| 5,435,282 A | 7/1995 | Haber et al. |
| 5,435,465 A | 7/1995 | El-Amin |
| 5,462,586 A * | 10/1995 | Sugiyama et al. ............... 96/13 |
| 5,485,828 A | 1/1996 | Hauser |

| | | | | | | |
|---|---|---|---|---|---|---|
| 5,496,411 | A | 3/1996 | Candy | 6,546,927 B2 | 4/2003 | Litherland et al. |
| 5,499,751 | A | 3/1996 | Meyer | 6,550,472 B2 | 4/2003 | Litherland et al. |
| D368,774 | S | 4/1996 | Py | 6,554,201 B2 | 4/2003 | Klimowecz et al. |
| 5,515,841 | A | 5/1996 | Robertson et al. | 6,554,801 B1 | 4/2003 | Steward et al. |
| 5,518,179 | A | 5/1996 | Humberstone et al. | 6,569,131 B1 | 5/2003 | Michael et al. |
| 5,529,055 | A | 6/1996 | Gueret | 6,569,387 B1 | 5/2003 | Furner et al. |
| D374,719 | S | 10/1996 | Py | 6,601,581 B1 | 8/2003 | Babaev |
| 5,584,823 | A | 12/1996 | Valberg | 6,612,302 B1 | 9/2003 | Rand |
| 5,586,550 | A | 12/1996 | Ivri et al. | 6,615,824 B1 | 9/2003 | Power |
| 5,588,564 | A | 12/1996 | Hutson et al. | 6,619,562 B2 | 9/2003 | Hamaguchi et al. |
| 5,607,410 | A | 3/1997 | Branch | 6,622,720 B2 * | 9/2003 | Hadimioglu ........... 128/200.16 |
| 5,613,957 | A | 3/1997 | Py | 6,629,646 B1 | 10/2003 | Ivri |
| 5,614,545 | A | 3/1997 | Martin et al. | 6,640,804 B2 | 11/2003 | Ivri et al. |
| 5,630,793 | A | 5/1997 | Rowe | 6,650,935 B1 | 11/2003 | Watmough |
| 5,641,004 | A | 6/1997 | Py | 6,651,650 B1 * | 11/2003 | Yamamoto et al. ..... 128/200.16 |
| 5,657,926 | A * | 8/1997 | Toda ...................... 239/102.2 | 6,659,364 B1 | 12/2003 | Humberstone et al. |
| 5,665,079 | A | 9/1997 | Stahl | 6,669,961 B2 | 12/2003 | Kim et al. |
| 5,685,869 | A | 11/1997 | Py | 6,676,034 B2 | 1/2004 | Tanaka et al. |
| 5,707,636 | A * | 1/1998 | Rodriguez et al. .......... 424/401 | 6,679,436 B1 | 1/2004 | Onishi et al. |
| 5,724,021 | A | 3/1998 | Perrone | 6,684,681 B1 | 2/2004 | Zombo |
| 5,730,723 | A | 3/1998 | Castellano et al. | 6,719,770 B2 | 4/2004 | Laufer et al. |
| 5,735,811 | A | 4/1998 | Brisken | 6,732,944 B2 | 5/2004 | Litherland et al. |
| 5,746,728 | A | 5/1998 | Py | 6,736,904 B2 | 5/2004 | Poniatowski et al. |
| 5,758,637 | A | 6/1998 | Ivri et al. | 6,740,107 B2 | 5/2004 | Loeb et al. |
| 5,807,357 | A | 9/1998 | Kang | 6,748,944 B1 | 6/2004 | Della Vecchia et al. |
| 5,823,428 | A | 10/1998 | Humberstone et al. | 6,761,286 B2 | 7/2004 | Py et al. |
| 5,838,350 | A | 11/1998 | Newcombe et al. | 6,789,741 B2 | 9/2004 | Varanasi et al. |
| 5,843,109 | A | 12/1998 | Mehta et al. | 6,814,071 B2 | 11/2004 | Klimowicz et al. |
| 5,855,322 | A | 1/1999 | Py | 6,851,626 B2 | 2/2005 | Patel et al. |
| 5,893,515 | A | 4/1999 | Hahn et al. | 6,854,662 B2 | 2/2005 | Chen |
| 5,894,841 | A * | 4/1999 | Voges .................... 128/203.12 | 6,863,224 B2 | 3/2005 | Terada et al. |
| 5,938,117 | A | 8/1999 | Ivri | 6,901,926 B2 | 6/2005 | Yamamoto et al. |
| D413,668 | S | 9/1999 | Mannberg et al. | 6,913,205 B2 | 7/2005 | Cornet et al. |
| 5,957,943 | A | 9/1999 | Vaitekunas | 6,921,020 B2 | 7/2005 | Ivri |
| 5,970,974 | A | 10/1999 | Van Der Linden et al. | 6,926,208 B2 | 8/2005 | Ivri |
| 5,996,903 | A | 12/1999 | Asai et al. | 6,946,117 B1 | 9/2005 | Schutt et al. |
| 5,997,518 | A | 12/1999 | Laibovitz et al. | 6,964,647 B1 | 11/2005 | Babaev |
| 6,008,468 | A | 12/1999 | Tanaka et al. | 6,969,165 B2 * | 11/2005 | Olsen .......................... 347/87 |
| 6,027,450 | A | 2/2000 | Brown et al. | 6,974,450 B2 | 12/2005 | Weber et al. |
| 6,039,565 | A | 3/2000 | Chou et al. | 6,976,969 B2 | 12/2005 | Messerly |
| 6,062,212 | A | 5/2000 | Davison et al. | 6,978,945 B2 | 12/2005 | Wong et al. |
| 6,083,922 | A | 7/2000 | Montgomery | 7,017,573 B1 | 3/2006 | Rasor et al. |
| 6,085,740 | A | 7/2000 | Ivri et al. | 7,040,549 B2 | 5/2006 | Ivri et al. |
| 6,135,427 | A | 10/2000 | Tsai | 7,066,398 B2 | 6/2006 | Borland et al. |
| 6,152,383 | A | 11/2000 | Chen | 7,081,757 B2 | 7/2006 | Unsworth et al. |
| 6,159,188 | A | 12/2000 | Laibovitz et al. | 7,083,112 B2 | 8/2006 | Ivri |
| 6,193,683 | B1 | 2/2001 | Ludin et al. | 7,104,463 B2 | 9/2006 | Litherland et al. |
| 6,221,038 | B1 | 4/2001 | Brisken | 7,108,197 B2 | 9/2006 | Ivri |
| 6,228,046 | B1 | 5/2001 | Brisken | 7,121,275 B2 * | 10/2006 | Noolandi et al. ........ 128/200.14 |
| 6,235,024 | B1 | 5/2001 | Tu | D533,658 S | 12/2006 | Collins, Jr. et al. |
| 6,254,579 | B1 | 7/2001 | Cogger et al. | 7,153,315 B2 | 12/2006 | Miller |
| 6,254,587 | B1 | 7/2001 | Christ et al. | 7,161,269 B2 | 1/2007 | Kayama et al. |
| 6,263,872 | B1 | 7/2001 | Schuster et al. | 7,168,633 B2 | 1/2007 | Wang et al. |
| 6,273,342 | B1 | 8/2001 | Terada et al. | D537,160 S | 2/2007 | Lowell |
| 6,336,917 | B1 * | 1/2002 | Berke ......................... 604/295 | 7,174,888 B2 | 2/2007 | Ivri et al. |
| 6,341,732 | B1 | 1/2002 | Martin et al. | 7,204,820 B2 | 4/2007 | Akahoshi |
| 6,357,671 | B1 | 3/2002 | Cewers | 7,229,028 B2 | 6/2007 | Chen et al. |
| 6,367,685 | B1 | 4/2002 | Jiang et al. | 7,314,187 B2 | 1/2008 | Hochrainer et al. |
| 6,387,671 | B1 | 5/2002 | Rubinsky et al. | 7,316,067 B2 | 1/2008 | Blakey |
| 6,394,363 | B1 | 5/2002 | Arnott et al. | 7,331,339 B2 | 2/2008 | Smith et al. |
| 6,398,737 | B2 | 6/2002 | Moore et al. | 7,357,133 B2 | 4/2008 | Goodchild |
| 6,398,766 | B1 | 6/2002 | Branch | 7,472,701 B2 | 1/2009 | Pfichner et al. |
| 6,423,040 | B1 | 7/2002 | Benktzon et al. | D597,206 S | 7/2009 | Collins, Jr. et al. |
| 6,425,888 | B1 | 7/2002 | Embleton et al. | 2001/0025190 A1 | 9/2001 | Weber et al. |
| 6,427,682 | B1 | 8/2002 | Klimowicz et al. | 2001/0049608 A1 | 12/2001 | Hochman |
| 6,442,423 | B1 | 8/2002 | Domb et al. | 2001/0056258 A1 | 12/2001 | Evans |
| 6,467,476 | B1 | 10/2002 | Ivri et al. | 2002/0016576 A1 | 2/2002 | Lee |
| 6,524,287 | B1 | 2/2003 | Cogger | 2002/0039502 A1 * | 4/2002 | Matsumoto et al. ......... 399/258 |
| 6,526,976 | B1 | 3/2003 | Baran | 2002/0043262 A1 | 4/2002 | Langford et al. |
| 6,530,370 | B1 | 3/2003 | Heinonen | 2002/0073989 A1 * | 6/2002 | Hadimioglu ........... 128/200.14 |
| 6,540,153 | B1 | 4/2003 | Ivri | 2002/0074362 A1 | 6/2002 | Py et al. |
| 6,540,154 | B1 * | 4/2003 | Ivri et al. ...................... 239/11 | 2002/0121285 A1 | 9/2002 | Poniatowski et al. |
| 6,543,443 | B1 * | 4/2003 | Klimowicz et al. .... 128/200.23 | 2002/0124843 A1 | 9/2002 | Skiba et al. |

| | | |
|---|---|---|
| 2002/0161344 A1 | 10/2002 | Peclat et al. |
| 2003/0032930 A1 | 2/2003 | Branch |
| 2003/0078551 A1 | 4/2003 | Hochrainer et al. |
| 2003/0114901 A1 | 6/2003 | Loeb et al. |
| 2003/0144594 A1 | 7/2003 | Gellman |
| 2003/0185892 A1 | 10/2003 | Bell et al. |
| 2003/0192532 A1 | 10/2003 | Hopkins |
| 2004/0010239 A1 | 1/2004 | Hochrainer et al. |
| 2004/0045547 A1 | 3/2004 | Yamamoto et al. |
| 2004/0050953 A1 | 3/2004 | Terada et al. |
| 2004/0082884 A1 | 4/2004 | Pal et al. |
| 2004/0164099 A1 | 8/2004 | Diestelhorst et al. |
| 2004/0176757 A1 | 9/2004 | Sinelnikov et al. |
| 2004/0186384 A1 | 9/2004 | Babaev |
| 2004/0256487 A1 | 12/2004 | Collins, Jr. et al. |
| 2005/0077315 A1 | 4/2005 | Bohdan et al. |
| 2005/0077392 A1 | 4/2005 | Geser et al. |
| 2005/0089545 A1 | 4/2005 | Kuwano et al. |
| 2005/0195598 A1 | 9/2005 | Dancs et al. |
| 2005/0199236 A1 | 9/2005 | Fink et al. |
| 2005/0240162 A1 | 10/2005 | Chen et al. |
| 2005/0244339 A1 | 11/2005 | Jauernig et al. |
| 2005/0261641 A1 | 11/2005 | Warchol et al. |
| 2005/0263608 A1 | 12/2005 | Ivri |
| 2005/0275310 A1 | 12/2005 | Ripoll |
| 2005/0279350 A1 | 12/2005 | Rasor et al. |
| 2006/0024374 A1 | 2/2006 | Gasco et al. |
| 2006/0057216 A1 | 3/2006 | Salamone et al. |
| 2006/0196518 A1 | 9/2006 | Hon |
| 2006/0201501 A1 | 9/2006 | Morrison et al. |
| 2006/0213503 A1 | 9/2006 | Borgschulte et al. |
| 2006/0258993 A1 | 11/2006 | Hochrainer et al. |
| 2007/0023547 A1 | 2/2007 | Borland et al. |
| 2007/0044792 A1 | 3/2007 | Ivri |
| 2007/0119968 A1 | 5/2007 | Collins, Jr. et al. |
| 2007/0119969 A1 | 5/2007 | Collins, Jr. et al. |
| 2008/0097359 A1 | 4/2008 | Hochrainer et al. |
| 2008/0142624 A1 | 6/2008 | Ivri |
| 2008/0164339 A1 | 7/2008 | Duru |
| 2008/0299049 A1 | 12/2008 | Stangl |
| 2008/0308096 A1 | 12/2008 | Borgschulte et al. |
| 2009/0025713 A1 | 1/2009 | Keller et al. |
| 2009/0114742 A1 | 5/2009 | Collins, Jr. |
| 2009/0149829 A1 | 6/2009 | Collins, Jr. |
| 2009/0192443 A1 | 7/2009 | Collins, Jr. |
| 2009/0212133 A1 | 8/2009 | Collins, Jr. |

FOREIGN PATENT DOCUMENTS

| | | |
|---|---|---|
| EP | 0 150 571 A1 | 8/1985 |
| EP | 0 150 571 B1 | 7/1988 |
| EP | 0 823 246 | 11/1998 |
| EP | 0933138 A2 | 3/2004 |
| GB | 558 866 | 1/1944 |
| GB | 558 866 A | 1/1944 |
| GB | 1 569 707 | 6/1980 |
| WO | WO 91/12687 A1 | 8/1991 |
| WO | WO 91/14468 | 10/1991 |
| WO | WO 94/13305 | 6/1994 |
| WO | WO 94/23788 | 10/1994 |
| WO | WO 9705960 | 2/1997 |
| WO | WO 97/12687 | 4/1997 |
| WO | WO 97/17933 | 5/1997 |
| WO | WO 99/17888 A1 | 4/1999 |
| WO | WO 00/18455 | 4/2000 |
| WO | WO 00/18455 A1 | 4/2000 |
| WO | WO 0066277 | 11/2000 |
| WO | WO 01/03645 | 1/2001 |
| WO | WO 01/03645 A2 | 1/2001 |
| WO | WO 01/19437 | 3/2001 |
| WO | WO 01/58236 | 8/2001 |
| WO | WO 02/28545 A1 | 4/2002 |
| WO | WO 02/055131 | 7/2002 |
| WO | WO 02/072169 A2 | 9/2002 |
| WO | WO 03/002045 | 1/2003 |
| WO | WO 03/002265 | 1/2003 |
| WO | WO 03002045 | 1/2003 |
| WO | WO 03002265 A1 | 1/2003 |
| WO | WO 03/026556 | 4/2003 |
| WO | WO 03097139 A1 | 11/2003 |
| WO | WO 2004/050065 | 6/2004 |
| WO | WO 2004/103478 A1 | 12/2004 |
| WO | WO 2004/105864 | 12/2004 |
| WO | WO 2006/006963 A2 | 1/2006 |
| WO | WO 2006/082588 A2 | 8/2006 |
| WO | WO 2008/015394 A1 | 2/2008 |

OTHER PUBLICATIONS

Aqueous Ophthalmic Spray as a Novel Method for Delivery of Artificial Tears to the Ocular Surface (JHU Ref. DM-3883), Inventors: Al-Abdulla, Nael A., Snyder, Lee; Web page www.hohpkinsmedicine.org/lbd/otl/3883.html; Feb. 10, 2004; Johns Hopkins Medicine; Technology Licensing Opportunities.

Bespak Drug Delivery Technologies, Web page www.bespak.com/drug_compliance.asp?id=7; viewed May 26, 2004.

Dhand, Rajiv M.D.; "Nebulizers That Use a Vibrating Mesh or Plate with Multiple Apertures to Generate Aerosol"; Respiratory Care Dec. 2002; vol. 47 No. 12; pp. 1406-1418.

HTTP://WWW1.MYSTICPHARMACEUTICALS.COM, Mystic Pharmaceuticals, Copyright 2004-2005.

Marco Fabrizio Saettone, Progress and Problems in Ophthalmic Drug Delivery, Business Briefing: Pharmatech 2002, pp. 1-6.

R. Gurny, H. Ibrahim, A. Aebi and P. Buri, Design and evaluation of controlled release systems for the eye, Journal of Controlled Release, vol. 6, Issue 1, Dec. 1987, pp. 367-373.

Linda Roach, Inside the Eye: Precision Drug Delivery, EyeNet Magazine, Jan. 2003.

Medical Instill Technologies, Inc. Brochure, MEDInstill, 2003.

Communication Relating to the Results of the Partial International Search Report of International Application No. PCT/US2008/001053, filed Jan. 25, 2008.

International Search Report for International Application No. PCT/US2008/001053 dated Aug. 27, 2008.

European Supplementary Search Report for European Application No. EP 04 75 3072 mailed on Feb. 27, 2009.

U.S. Appl. No. 11/698,438, filed Jan. 26, 2007, James F. Collins, Jr. et al.

U.S. Appl. No. 11/698,647, filed Jan. 26, 2007, James F. Collins, Jr. et al.

U.S. Appl. No. 12/287,141, filed Oct. 6, 2008, James F. Collins, Jr.

U.S. Appl. No. 12/287,147, filed Oct. 6, 2008, James F. Collins, Jr.

U.S. Appl. No. 12/287,149, filed Oct. 6, 2008, James F. Collins, Jr.

U.S. Appl. No. 12/287,150, filed Oct. 6, 2008, James F. Collins, Jr.

Office Action mailed on Feb. 16, 2010 regarding U.S. Appl. No. 11/698,438.

U.S. Appl. No. 12/650,008, filed Dec. 30, 2009, James F. Collins, Jr. et al.

Halberg, G.P., et al., "Drug delivery systems for topical ophthalmic medication," Ann. Ophthalmol. vol. 7, No. 9, Sep. 1975, pp. 1199-1209.

March, W.F., et al., "Abstract of Duration of effect of pilocarpine gel," Arch Ophthalmol, vol. 100, No. 8, Aug. 1982, pp. 1270 1271, one page.

Prince, D.S., "Respiratory arrest following first dose of timolol ophthalmic solution," Chest, vol. 84, No. 5, 1983, pp. 640-641.

Brown, M.M., et al., Abstract of "Improper topical self-administration of ocular medication among patients with glaucoma," Can. J. Ophtalmol. vol. 19, No. 1, Feb. 1984, pp. 2-5 available at www.pubmed.gov, date of availability unknown, one page.

Kumar, V., et al., "Systemic absorption and cardiovascular effects of phenylephrine eyedrops," Am. J. Ophthalmol. vol. 99, No. 22, Feb. 1985, pp. 180-184.

Brown, R.H., et al., "Creating smaller eyedrops by reducing eyedropper tip dimensions," Am. J. Ophthalmol., vol. 99, Apr. 1985, pp. 460-464.

Fraunfelder, F., et al., "Systemic adverse reactions to glaucoma medicationsm," Int. Ophthalmol. Clin. vol. 29, No. 3, Fall 1989, pp. 143-146.

Winfield, A.J., et al., "A study of the causes of non-compliance by patents prescribed eyedrops," Br. J. Ophthalmol., vol. 74, No. 8, 1990, pp. 477-480.

Salminen, L., "Abstract of Review: systemic absorption of topically applied ocular drugs in humans," J. Ocul. Pharmacol., vol. 6, No. 3, pp. 243-249, one page.

Smith, S.E., "Eyedrop installation for reluctant children," Br. J. Ophthalmol., vol. 75, 1991, pp. 480-481.

Burns, E., et al., "Practical problems with eye drops among elderly ophthalmology outpatients," Age and Ageing, Vo. 21, 1992, pp. 168-170.

Stevens, J.D., et al., "Survey of the contamination of eyedrops of hospital in patients and recommendations for the changing of current practice in eyedrop dispensing," Br. J. Ophthalmol., Vo. 76, 1992, pp. 36-38.

Siovin, E.M. et al., "*Bioadhesives in Ocular Drug Delivery,*" Biopharmaceutics of Ocular Drug Delivery, Edman, P., ed., CRC Press, Inc., Boca Raton, FL, 1993, chap.9, pp. 145-157.

Van Ooteghem, M., *Biopharmaceutics Ocular Drug Delivery*, Edman, P., ed., CRC Press, Inc., Boca Raton, FL 1993, pp. 27-42, 174-176.

Schoenwald R., "Pharmacokinetics in Ocular Drug Delivery," Edman P, ed. Biopharmaceutics of Ocular Drug Delivery, Boca Raton: CRC Press Inc., 1993, Chapter 10, pp. 159-190.

Hughes, F, et al., "Abstract of Systemic and local tolerability of ophthalmic drug formulations, An update", Drug Saf., 1993, vol. 8, pp. 365-380, one page.

Flach, A., "Abstract of Systemic toxicity. Associated with topical ophthalmic medications," J. Fla. Med. Assoc., 1994; vol. 81, pp. 256-260, one page.

O'Donoghue, E., "Beta blockers and the elderly with glaucoma: are we adding insult to injury?," Br. J. Ophthalmol., vol. 79, 1995, pp. 794-796.

Leino, M., et al., "Delivery Systemic Absorption of Topical Glaucoma Drugs," *Ocular Therapeutics and Drug Delivery*, Reddy, I.K., Technomic Publishing Co., Inc., Lancaster, PA, 1996, p. 255.

Joshin, A., "Microparticulates as an Ocular Delivery System," *Ocular Therapeutics and Drug Delivery*, Reddy, I.K., Technomic Publishing Co., Inc., Lancaster, PA, 1996, chap. 15, pp. 441-457.

Kahn, M. A., et al., "Polymers in Ophthalmic Drug Delivery Systems," *Ocular Therapeutics and Drug Delivery*, published by Technomic Publishing Co., Inc., Lancaster, PA, 1996, chap. 14, pp. 405-431.

Gangrade, N.K., et al., "Topical ophthalmic formulations: Basic considerations," Reddy IK, ed. Ocular therapeutics and drug delivery a multi-disciplinary approach. Lancaster: Technomic, 1996, Chapter 13, p. 377.

Diamond, J., "Systemic adverse effects of topical ophthalmic agents. Implications for older patients," Drugs Aging, 1997, vol. 11, No. 5, pp. 352-360, one page.

Velez, Gisela, et al., "New Developments in Sustained Release Drug Delivery for the Treatment of Intraocular Disease," Br. J. Ophthalmol., vol. 83, Nov. 1999, pp. 1225-1229, available at http://bjo.bmjjournals.com/cgi/content/full/83/11/1225 as of Jan. 16, 2006, 16 pages.

Wakayama, Nobuko I., et al., "Magnetic Acceleration of Inhaled and Exhaled Flows in Breathing," Jap. Journ. Appl. Phys., vol. 39, Part 2, No. 3A/B, Mar. 15, 2000, pp. L262-L264.

Sica, Domenic A., "Ophthalmically Administered β Blockers and their Cardiopulmonary Effects," Journal of Clinical Hypertension, Vol. III, No. III., May-Jun. 2001, pp. 175-178 and 182.

Kumar, M.T. et al., "Novel therapeutic approaches for uveitis and retinitis," J. Pharm. Pharmaceut. Sci., vol. 4, No. 3, 2001, pp. 248-254.

Macha et al., "Overview of ocular drug delivery," Mitra A.K. ed., Ophthalmic drug Delivery Systems, 2nd ed. Marcel Dekker, Inc., New York, New York, 2003, p. 8.

Van Santvliet, Luc., et al., "Determinants of Eye Drop Size," Survey of Ophthalmology, vol. 49, No. 2., Mar.-Apr. 2004, pp. 197-212.

Lee, S., et al., Abstract of "A new therapy concept with a liposome eye spray for the therapy of the "dry eye": First clinical results of a statistical analysis of a long-term study," regarding Sep. 26, 2004 meeting held in Berlin 102$^{nd}$ Jahresteagung der DOG Deutsche Ophthalmologische Gesellschaft e.V. published by gms, available at http://www.egms.de/en/meetings/dog2004/04dog064.shtml as of Oct. 27, 2005, 2 pages.

Kahn, Monte, "Bioavailability of vitamin $B_{12}$ using a small-volume nebulizer ophthalmic drug delivery system," Clinical and Experimental Ophthalmology, vol. 33, 2005, pp. 402-407.

Tattersall, C., et al., Abstract of "Resting pulse rate in a glaucoma clinic: the effect of topical and systemic beta-blocker usage," Eye, Apr. 1, 2005 available at http://www.ncbi.nlm.nih.gov/entrez/query.fcgi?cmd=Retrieve&db=pubmed&dopt=Abstract . . . as of Oct. 17, 2005, 1 page.

Abelson, Mark B., et al., "Thinking Outside the Eyedropper," Review of Ophthalmology, Sep. 2005, pp. 78-80.

Author unknown, "Violight™—Frequently Asked Questions" available at http://www.violight.com as of Oct. 12, 2005, 1 page.

Author unknown, "Violight™—Shop Violight" available at http://www.violight.com as of Oct. 12, 2005, 1 page.

http://images.businessweek.com/ss/05/06/idea2005/source/115.htm as of Oct. 12, 2005, 1 page.

Kesner, J., "Guarantee clean hygiene" Sep. 8, 2005 article available at http://www.violight.com as of Oct. 12, 2005, 1 page.

Audia, et al., "Close your eyes now, make a wish!" advertisement, available at http://www.wveyes.com/Tears%20Again%20Lipisome%20Spray.htm as of Oct. 27, 2005, one page.

Author unknown, "Tears Again Lipisome" advertisement, available at http://www.aclens.com/da.asp?ID=29&Mode=Enlarge as of Oct. 27, 2005, one page.

Lee, S., et al., Abstract of "A new therapy concept for the treatment of dry eye—the usefulness of phospholipid liposomes," Klin Monatsbl Augenheilkd., vol. 221, No. 10, Oct. 2004, pp. 825-836 available at http://www.ncbi.nlm.nih.qov/entrez/query.fcqi?cmd=Retrieve&db=pubmed&dopt=Abstract . . . as of Oct. 27, 2005, 2 pages.

Zhu, Shengwei, et al., Abstract of "Study on inhalation region by means of CFD analysis and experiment," Building and Environment, vol. 40, No. 10, Oct. 2005, pp. 1329-1336, available at http://www.sciencedirect.com/science?_ob=ArticleURL&_udiB6V23-4F4WYM5-1&_us . . . as of Apr. 12, 2008, 2 pages.

Anthony, T. Renee, et al., "CFD Model for a 3-D Inhaling Mannequin: Verification and Validation," Annals of Occupational Hygiene, vol. 50, No. 2, 2006, pp. 157-173, available at http://annhyg.oxfordjournals.org/cgi/content/full/50/2/157 as of Apr. 12, 2008, 22 pages.

Collins, James F., et al., "Mist Delivery of Eye Medication to the Anterior Segment," Amer. J. Ophthalmol., vol. 144, No. 1, Jul. 2007, pp. 137-139.

Author unknown, "Become an Expert in Spirometry" available at http://www.spirxpert.com/brrespuk/penetration.htm as of Apr. 16, 2008, 2 pages.

Author unknown, "electronic aerosol technology," made available by The Technology Partnership plc at http://www.ttp.com/technology/microdevices/discpump/ as or Apr. 25, 2008, one page.

Author unknown, "Protein and Peptide Drug Delivery to the Eye," source unknown, date of publication unknown, p. 479.

Xia, Wei, et al., "A Potential Application of a Piezoelectric Atomizer for Ophthalmic Drug Delivery," BOB 2007, vol. 4, No. 1, 2007, pp. 9-17.

Shen, S.C., "A New Cymbal-Shaped High Power Microactuator for Nebulizer Application," Microelectronic Engineering, 2009, pp. 1-9.

Author unknown, "Visine® Pure Tears: A Preservative-free Formula in a Multi-dose Bottle," Refractive Eyecare, Sep. 2005, pp. 24 and 26.

Author unknown, "Violight™—How it Works" available at http://www.violight.com as of Oct. 12, 2005, 1 page.

* cited by examiner

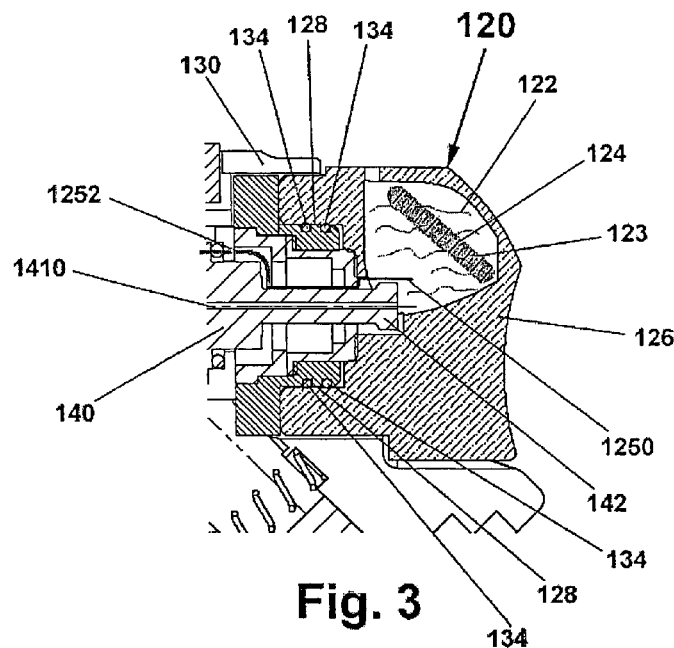
Fig. 3
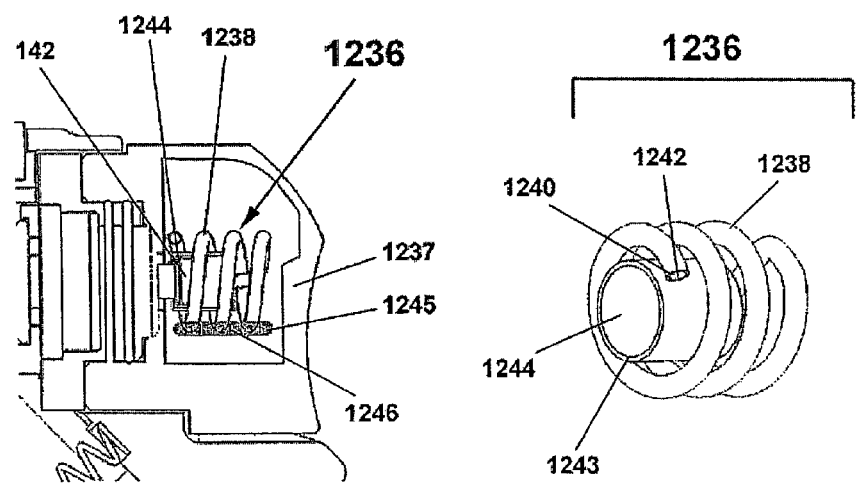
Fig. 7
Fig. 8

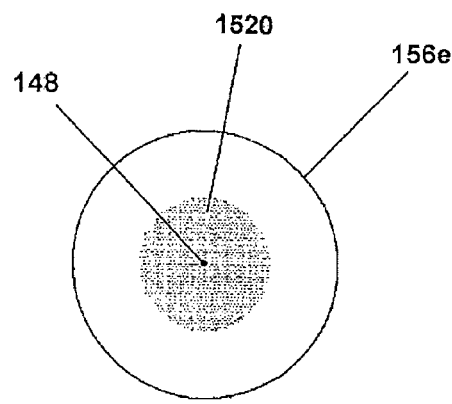
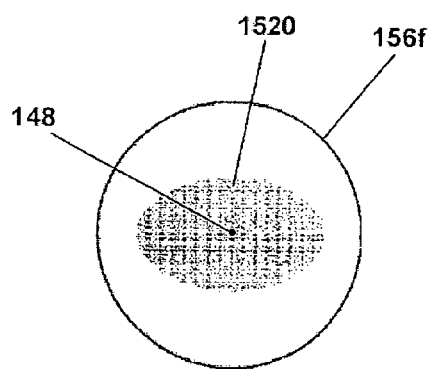
Fig. 13a Fig. 13b
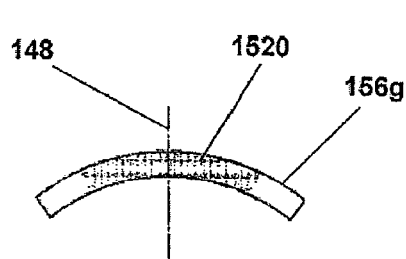
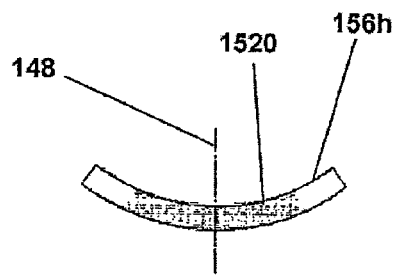
Fig. 13c Fig. 13d
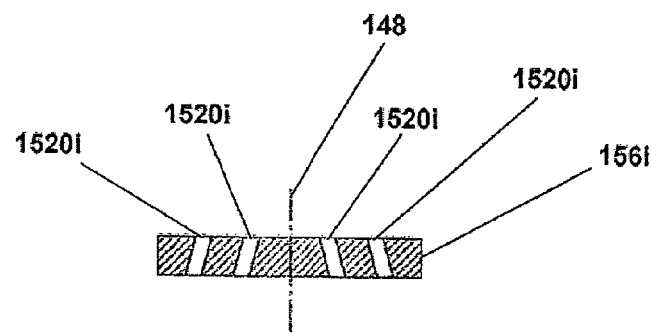
Fig. 13e

OPHTHALMIC DRUG DELIVERY SYSTEM

CROSS REFERENCE TO RELATED APPLICATIONS

The present application claims priority from U.S. Provisional Patent Application Ser. No. 60/471,883, filed May 20, 2003 and from U.S. Provisional Patent Application Ser. No. 60/485,305, filed Jul. 3, 2003.

FIELD OF THE INVENTION

The present invention relates to drug delivery devices for dispensing liquid as an aerosol or atomized mist and, more particularly, for dispensing medicaments to the eye.

BACKGROUND OF THE INVENTION

Presently, conventional eye drops are the standard means of delivering medicaments to the eye. This means of ophthalmic drug delivery, however, has numerous problems. For example, the average eye drop (approximately 50 micro liters) far exceeds the eye's capacity (7 micro liters in the pre-corneal tear film and a maximum of about 30 micro liters in the lower cul-de-sac) effectively destabilizing and stripping the natural tear film. This results in a brief period of massive over-dosage, which is quickly cleared by reflex lacrimation, blinking and nasolacrimal drainage, resulting in sub-therapeutic drug levels until the next medication application. This approach represents very inefficient pharmacokinetics. Far smaller volumes of medicament (approximately one tenth of a conventional drop) are desirable and are, in fact, retained by the eye and "bio-available" for a substantially longer time.

Attempts to prolong ocular contact time by various adaptations, such as the use of particulate suspensions, have led to other drawbacks including ocular irritation and excessively slow drug release. Ointments and gels, though providing prolonged contact time, create obvious visual disturbances.

Further, local irritations and toxicities often result from the regular use of eye drops. These situations vary widely depending on the pharmacologic agent, preservatives and other additives being used, but this is clearly a very non-physiologic and inefficient system of medication administration. Chronic use of eye drops for such conditions as glaucoma and prolonged infections and inflammations can, in fact, cause substantial morbidity. Additionally, serious and even fatal reactions to sympathomimetic and beta-adrenergic blocking agents have occurred as a result of systemic absorption of eye drops via nasolacrimal drainage.

Besides the above issues, there are a great many difficulties that patients experience with the mechanics of eye drop administration. Elderly patients, the largest group of eye drop users, often have hand-eye coordination problems, tremors or arthritis, affecting the hands and/or the cervical spine, making eye drop administration difficult if not impossible. Many users report that they have trouble keeping track of their regimens and often repeat doses or miss them entirely, suffering potential consequences in either event. Further, pediatric patients, often unable to comprehend the reasons and benefits behind the administration of eye medication, often fight such application, typically resulting in underdosing due to the patient's attempts to prevent the eye drops from being administered, or overdosing, as a result of the administrator's attempt to ensure that sufficient dosage is being applied.

Additionally, very few regular users of eye drops, in any age group, actually observe the ideal technique of administration, including tear sac compression, to minimize excretory loss and potential systemic absorption. It is sometimes difficult to tell if the drop was properly instilled. Direct application to the cornea can result in the drop "bouncing" from the eye with little or no benefit.

Regular eye drop users commonly report using several drops which "missed" the eye until they are sure they properly instilled the drop. Also, many eye drop bottles are fabricated in such a way that loss is unavoidable as soon as the dropper is tilted. Finally, a significant number of regular users put another drop or two in the eye "just to be sure". All of the above represent needless waste of expensive medication (many glaucoma medications cost $70-$80 for a 5 ml bottle) and also increased the risk of side effects, while actually reducing the therapeutic benefit.

The ophthalmic literature is rife with references to the need for a better means of ophthalmic drug delivery. With an estimate of 25 million users of eye drops in the United States alone, the magnitude of the public health issue is considerable. Accordingly, a new means of ophthalmic drug delivery is needed.

The concept of "spraying" medicated solutions on to the eye is not a new one. A number of devices have been conceptualized and developed for this purpose. Various means of atomizing and propelling solutions including mechanical pumps, gas-propelled jets and pistons, etc. which have inherent drawbacks relating to difficulties with calibrating the flow velocity, volume and particle size of the emitted spray. See, for example, U.S. Pat. Nos. 3,170,462; 5,630,793; and 6,062,212.

It is hypothesized that the generated mist will expand and "therapeutically alter" but not significantly disrupt the physiologic tear film allowing for a more natural process in the transmission of therapeutic agents to the surface and the interior of the eye. A much smaller volume of solution can be administered below the blink and lacrimation thresholds, allowing for a prolonged time of application. The aggregate administration of a drug in thousands of 5-micron particles should significantly exceed that of a single eye drop, leading to greater concentrations of the drug (bioavailability). Furthermore, the surface tension of a standard drop is a barrier to "mixing" and tear film incorporation. This problem is expected to be avoided with micronebulization.

An additional benefit to mist administration of eye medications is the avoidance of dropper bottle contamination which commonly occurs from contact with the eyelid. In the professional office setting, this problem has led to many documented epidemics of viral keratoconjunctivitis. During medication administration via a dropper bottle to a patient with viral keratoconjunctivitis, the bottle tip may inadvertently touch the eye or eyelid of the affected patient, transferring the virus to the bottle tip. Subsequent medication administrations to other patients using the same dropper bottle transmits the virus to those patients.

Some of the beneficial features of an ophthalmic medication spray dispenser include the following: great ease of use; can be used in any "attitude" (i.e. with patient sitting, erect, lying down, head tilted back, etc.); abbreviated treatment cycle as compared to eye drop usage; improved bioavailability/efficacy; improved safety (reduced local and systemic side effects); improved sterility; increased compliance due to ease of use and "alert" systems; possibility of singular efficacy in the treatment of certain vision threatening infections; conservation of material (reduced volume, diminished waste/loss); and system (fixation target to help ensure proper application).

It would be beneficial to provide a system for applying the desired small amounts (7 to 10 micro liters) of optical medication, along with at least some of the above-listed beneficial features, while eliminating the drawbacks associated with previous means of drug delivery.

BRIEF DESCRIPTION OF THE INVENTION

Briefly, the present invention provides a fluid atomizer comprising a body having a proximal end and a distal end. A removable reservoir is connected to the body, wherein the reservoir contains a fluid disposed therein. A discharge plate is disposed at the distal end, wherein the discharge plate includes a plurality of openings extending therethrough. The atomizer further comprises propulsion means for transmitting the fluid from the reservoir to the discharge plate and through the plurality of openings, wherein transmission of the fluid through the plurality of openings atomizes the fluid.

Also, the present invention provides a fluid atomizer comprising a body having a proximal end and a distal end. A removable reservoir is connected to the body, wherein the reservoir contains a fluid disposed therein. A discharge plate is disposed at the distal end, wherein the discharge plate includes a plurality of openings extending therethrough. The atomizer further comprises propulsion means for transmitting the fluid from the reservoir to the discharge plate and through the plurality of openings, wherein transmission of the fluid through the plurality of openings atomizes the fluid. The atomizer also includes a system controller electronically connected to the propulsion means, wherein the system controller controls operation of the propulsion means.

Further, the present invention provides a fluid atomizer comprising a body having a proximal end and a distal end. A removable reservoir is connected to the body, wherein the reservoir contains a fluid disposed therein. A discharge plate is disposed at the distal end, wherein the discharge plate includes a plurality of openings extending therethrough. The atomizer further comprises propulsion means for transmitting the fluid from the reservoir to the discharge plate and through the plurality of openings, wherein transmission of the fluid through the plurality of openings atomizes the fluid. The atomizer also includes a means for spacing the discharge plate a predetermined distance from a target.

Additionally, the present invention provides a fluid atomizer comprising a body having a proximal end and a distal end. A removable reservoir is connected to the body, wherein the reservoir contains a fluid disposed therein. A discharge plate is disposed at the distal end, wherein the discharge plate includes a plurality of openings extending therethrough. The atomizer further comprises propulsion means for transmitting the fluid from the reservoir to the discharge plate and through the plurality of openings, wherein transmission of the fluid through the plurality of openings atomizes the fluid. The atomizer also includes a system controller electronically connected to the propulsion means, wherein the system controller controls operation of the propulsion means. The atomizer also includes a means for adjusting operation of the propulsion means to adjust an amount of the fluid transmitted across the discharge plate, wherein the means for adjusting operation of the propulsion means are operatively connected to the system controller.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain features of the invention. In the drawings:

FIG. 3 is an enlarged side profile view of a first embodiment of a fluid reservoir connected to the device.

FIG. 5 is a side profile view of the first embodiment of the fluid reservoir shown in FIG. 3, having been removed from the device.

FIG. 6 is an enlarged side profile view of a second embodiment of a fluid reservoir.

FIG. 7 is an enlarged side profile view of a third embodiment of a fluid reservoir.

FIG. 8 is a perspective view of the reservoir of FIG. 7.

FIG. 9 is an enlarged side view, in section, of a prime mover inserted into the device.

FIG. 10 is an enlarged exploded perspective view of a nozzle assembly of the device.

FIG. 11 is an enlarged side view, in section, of the nozzle assembly of the device.

FIG. 12*a* is an enlarged partial sectional view of a first embodiment of the mesh plate of the nozzle assembly.

FIG. 12*b* is an enlarged partial sectional view of a second embodiment of the mesh plate of the nozzle assembly.

FIG. 12*c* is an enlarged partial sectional view of a third embodiment of the mesh plate of the nozzle assembly.

FIG. 12*d* is an enlarged partial sectional view of a fourth embodiment of the mesh plate of the nozzle assembly.

FIG. 13*a* is a top plan view of a first embodiment of a mesh plate.

FIG. 13*b* is a top plan view of a second embodiment of a mesh plate.

FIG. 13*c* is a side view, in section of a third embodiment of a mesh plate.

FIG. 13*d* is a side view, in section, of a fourth embodiment of a mesh plate.

FIG. 13*e* is an enlarged partial sectional view of a fifth embodiment of a mesh plate.

FIG. 14 is a perspective view of the device showing an optional dosage adjustment feature.

FIG. 15*a* is a perspective view of the device showing a first embodiment of the dosage adjustment feature.

FIG. 15*b* is a perspective view of the device showing a second embodiment of the dosage adjustment feature.

FIG. 15*c* is a perspective view of the device showing a third embodiment of the dosage adjustment feature.

FIG. 16 is a top plan view showing the targeting device of FIG. 14.

FIG. 17*a* is a schematic view of a first embodiment of a targeting mechanism showing the device too close to the target.

FIG. 17*b* is a schematic view of the first embodiment of the targeting mechanism showing the device a correct distance from the target.

FIG. 17*c* is a schematic view of the first embodiment of the targeting mechanism showing the device too far from the target.

FIG. 18*a* is a schematic view of a second embodiment of a targeting mechanism showing the device too close to the target.

FIG. 18*b* is a schematic view of the second embodiment of the targeting mechanism showing the device a correct distance from the target.

Figure 18A:
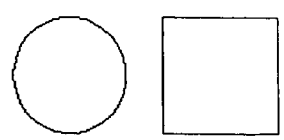
Figure 18B:
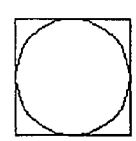
Figure 18C:
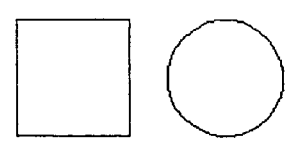

FIG. 18c is a schematic view of the second embodiment of the targeting mechanism showing the device too far from the target.

Figure 19A:

FIG. 19a is a schematic view of a third embodiment of a targeting mechanism showing the device too close to the target.

Figure 19B:
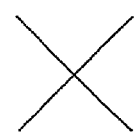

FIG. 19b is a schematic view of the third embodiment of the targeting mechanism showing the device a correct distance from the target.

Figure 19C:

FIG. 19c is a schematic view of the third embodiment of the targeting mechanism showing the device too far from the target.

Figure 20A:
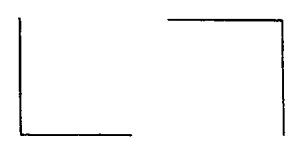

FIG. 20a is a schematic view of a fourth embodiment of a targeting mechanism showing the device too close to the target.

Figure 20B:
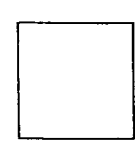

FIG. 20b is a schematic view of the fourth embodiment of the targeting mechanism showing the device a correct distance from the target.

Figure 20C:
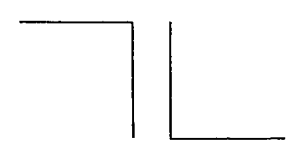

FIG. 20c is a schematic view of the fourth embodiment of the targeting mechanism showing the device too far from the target.

Figure 21A:
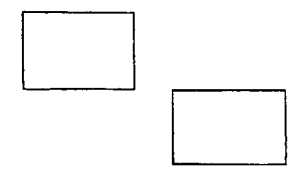

FIG. 21a is a schematic view of a fifth embodiment of a targeting mechanism showing the device too close to the target.

Figure 21B:

FIG. 21b is a schematic view of the fifth embodiment of the targeting mechanism showing the device a correct distance from the target.

Figure 21C:
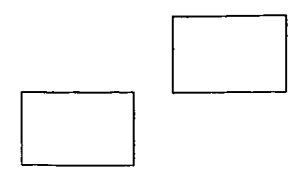

FIG. 21c is a schematic view of the fifth embodiment of the targeting mechanism showing the device too far from the target.

Figure 22A:
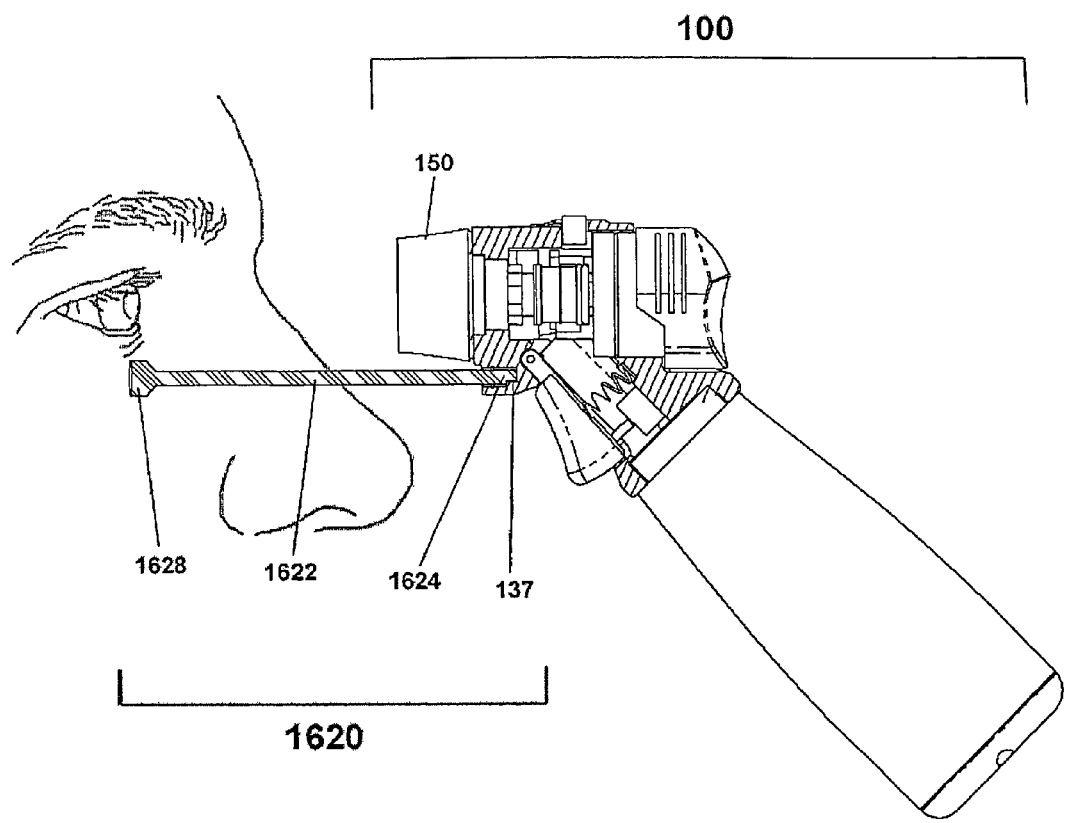

FIG. 22a is a side elevational view of a mechanical targeting device according to the present invention.

Figure 22B:
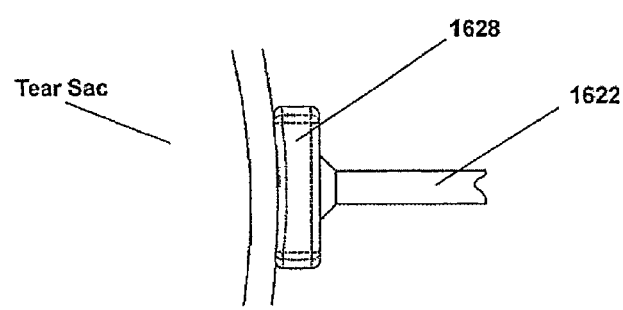

FIG. 22b is a top plan view of a proximal end of the mechanical targeting device shown in FIG. 22a, being used on a patient.

Figure 23:
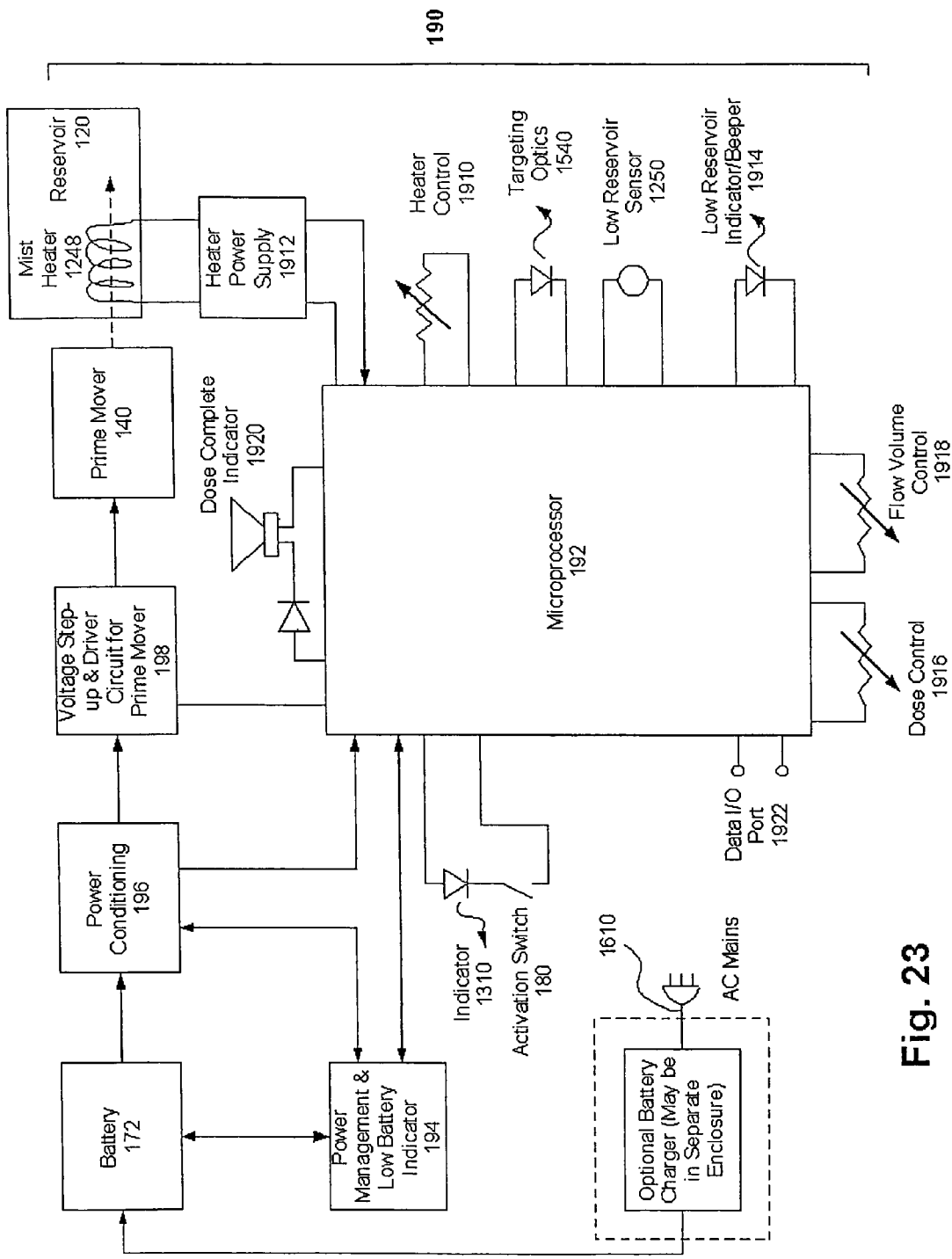

FIG. 23 is a schematic view of an electronic control system for the device.

Figure 24:
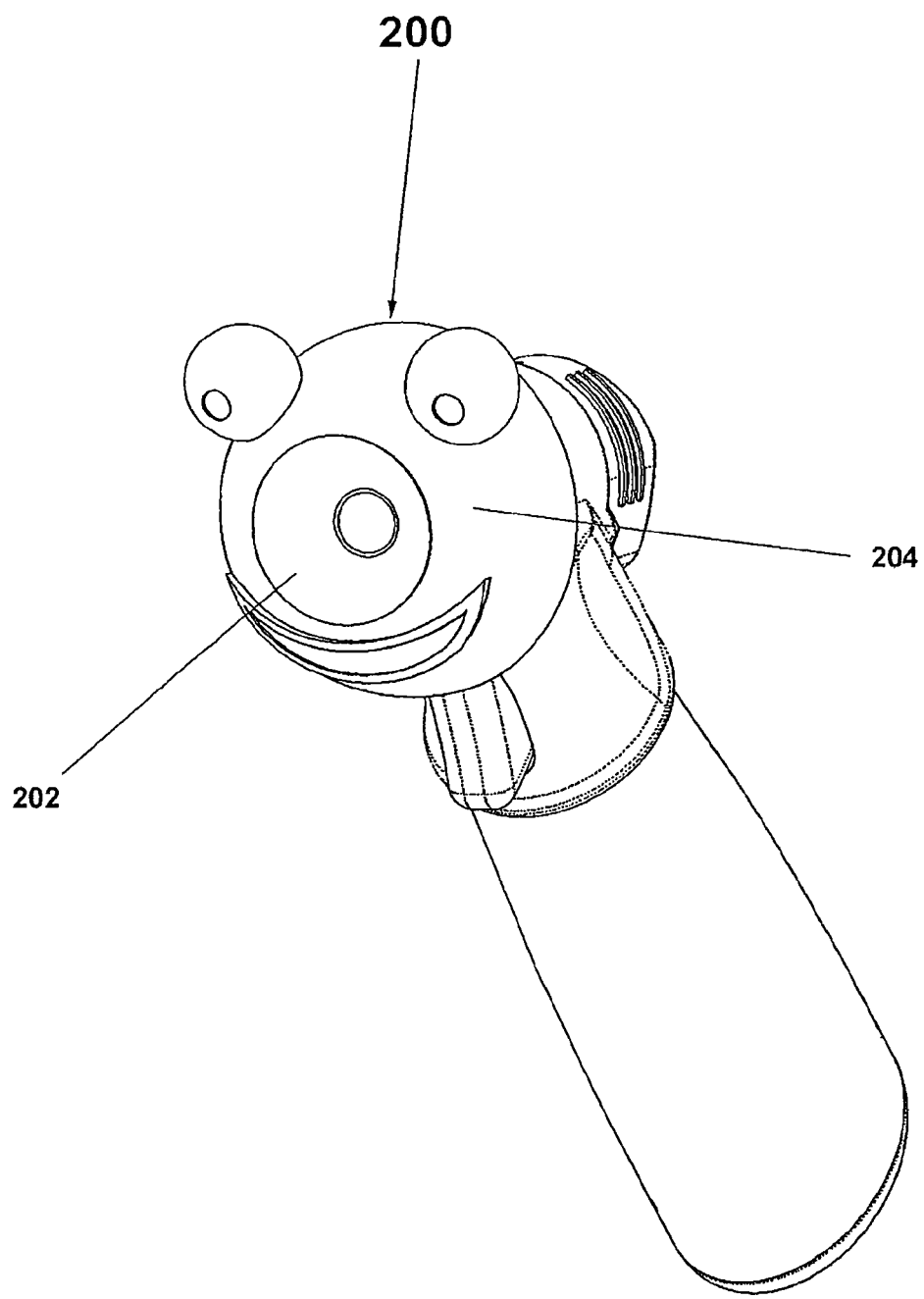

FIG. 24 is a perspective view of an alternative embodiment of the device according to the present invention.

Figure 25:
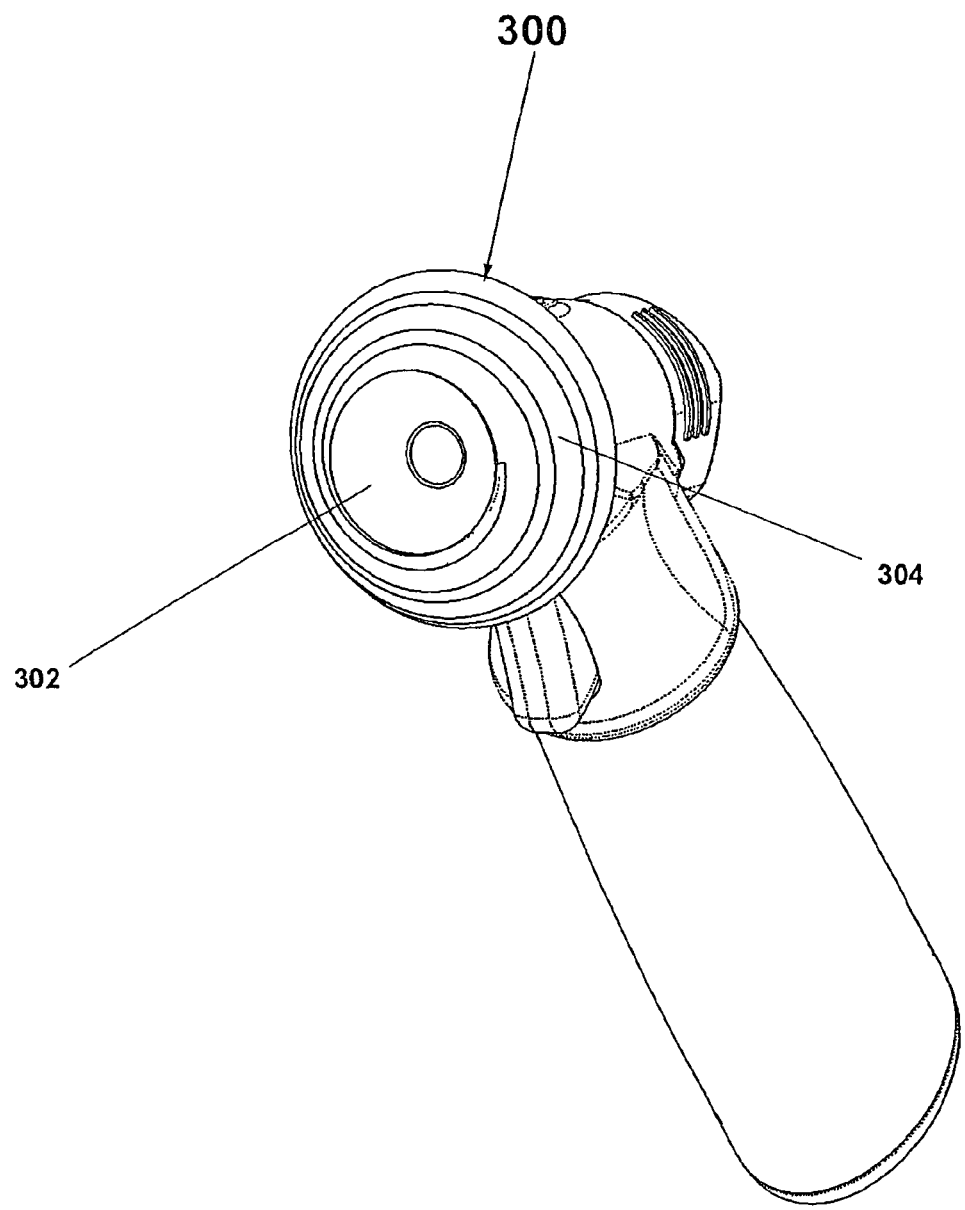

FIG. 25 is a perspective view of another alternative embodiment of the device according to the present invention.

Figure 26:
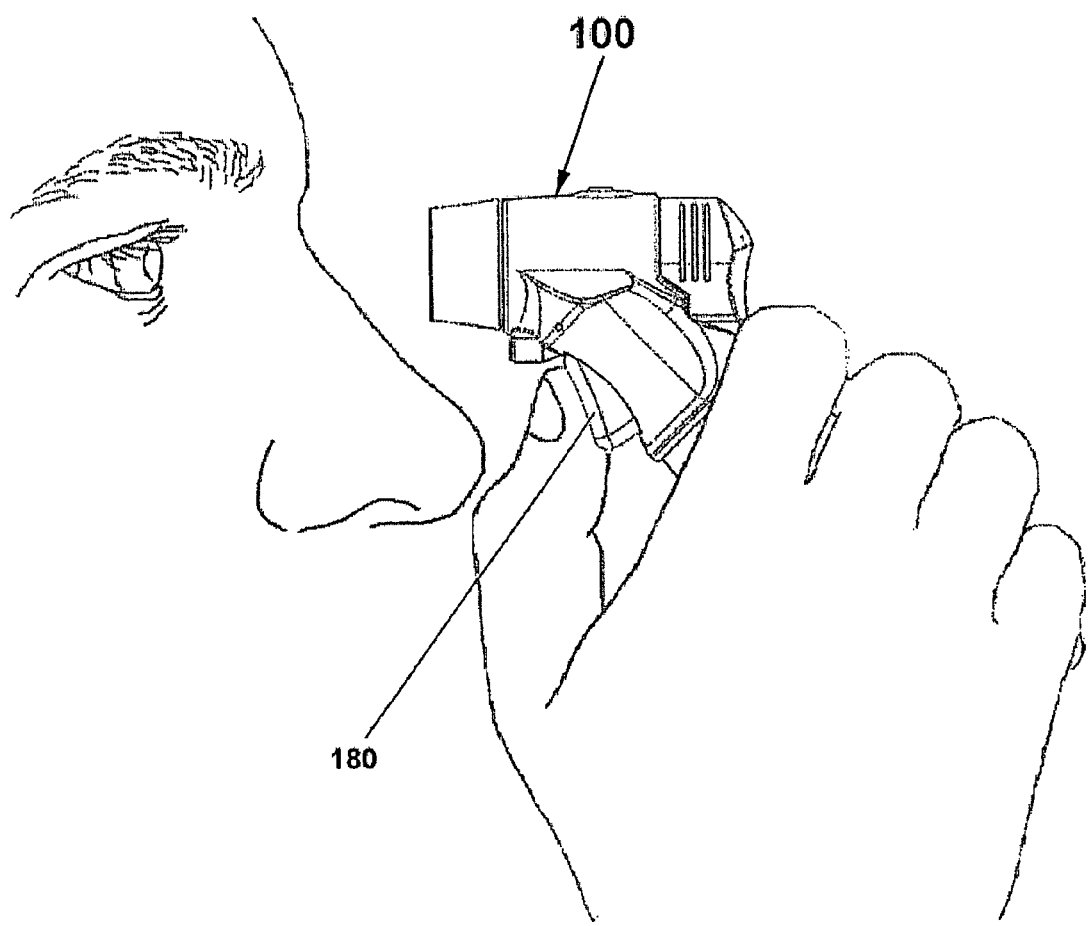

FIG. 26 is a perspective view showing self-administration of medication using the device.

Figure 27:
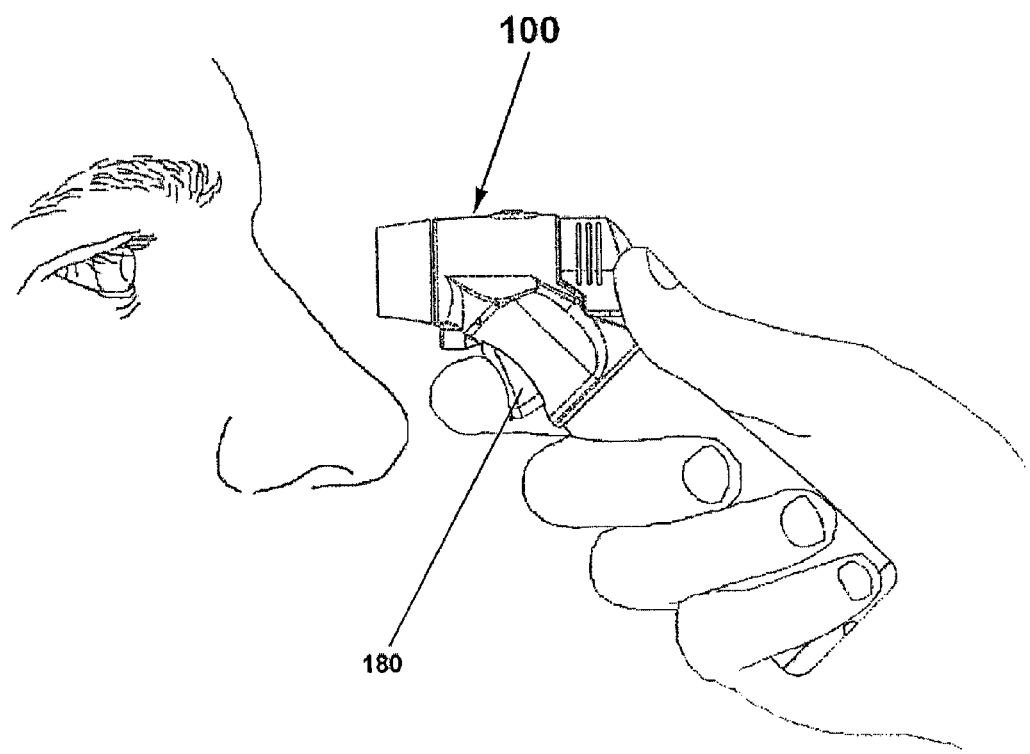

FIG. 27 is a perspective view showing administration of medication by one person to another using the device.

DETAILED DESCRIPTION OF THE INVENTION

Certain terminology is used in the following description for convenience only and is not limiting. As used herein, the term "distal" is meant to mean the discharge end of the inventive device and the term "proximal" is meant to mean the end of the inventive device held by user. The terminology includes the words above specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

The present invention provides a novel device and method for ophthalmic drug delivery. In preferred embodiments, the present invention provides a small, hand-held, battery or AC powered device that nebulizes liquid eye medications into a fine mist. The mist from the device is directed at the eye to be treated and the drug is delivered via the mist.

A preferred means of forming the mist is by ultrasound energy generated by a piezoelectric transducer or other suitable piezo device. A small plume of nebulized solution is generated, consisting of particles measuring what is believed to be an average of about five microns in diameter. The volume of each emission is dependent on the rate of mist generation (typically measured in micro liters per second) as well as the duration of the operation of the device, which may be easily varied by using an electronic control circuit. The shape, dimensions and focus of the emitted mist are proportioned for delivery to the human eye. The momentum of the mist is subliminal to the ocular blink and lacrimation reflexes and may also create a soothing sensation in the eye. The device is equally efficient when used in any "attitude" from a natural, upright head posture to leaning forward or lying back. Application time is significantly abbreviated compared to eye drop usage, which typically requires several maneuvers and careful attention to detail to ensure proper administration.

One preferred embodiment of the invention is now described with reference to FIGS. 1 and 2, which show a hand held device 100 that directs a mist of drug to an eye for treatment. As will be described in more detail below, the device 100 includes a vial or reservoir 120 of the fluid to be delivered to the eye, such as a drug. The user holds the device 100 and, by operating an activation switch, causes the device 100 to generate a mist of the liquid, which is discharged from the head portion 110 of the device 100. The user simply aims the head of the device at the target eye to allow the mist to contact the eye.

Figure 1:
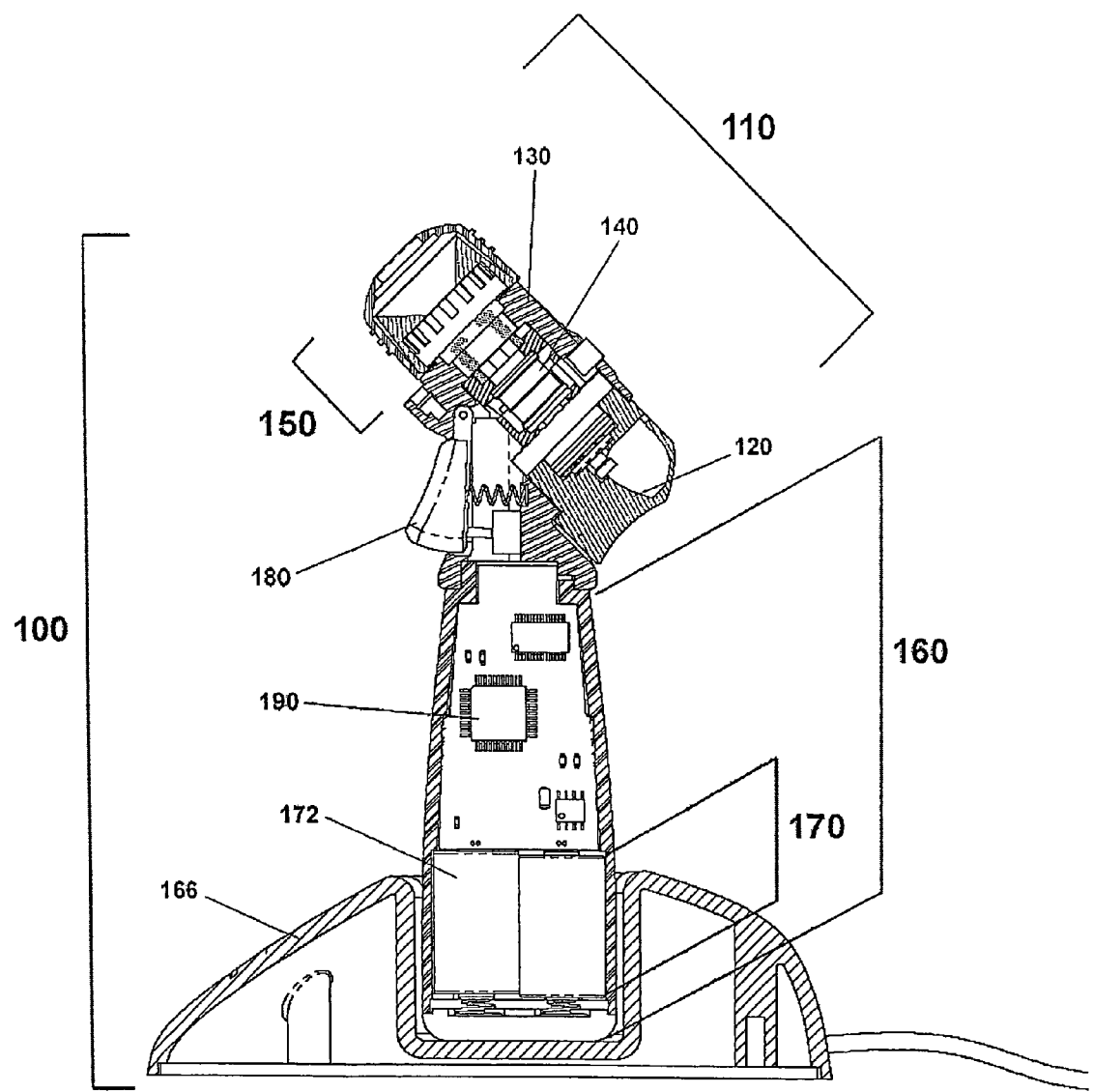
FIG. 1 is a side elevational view, partially broken away, of a mist spraying device according to a first embodiment of the present invention.
Figure 2:
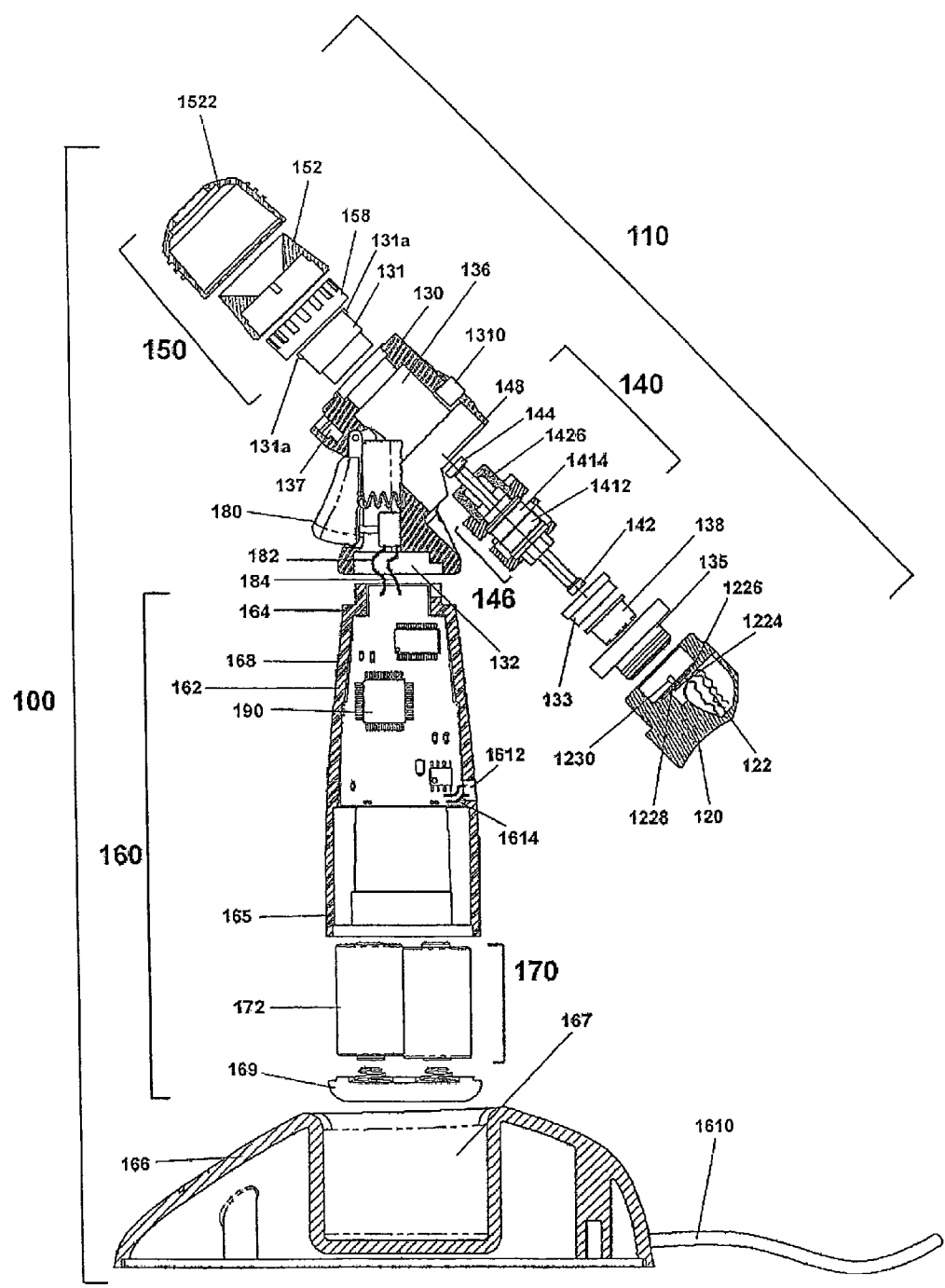
FIG. 2 is an exploded view of the device of FIG. 1.

Referring to FIGS. 1 and 2, the major components of the device 100 are shown. The components include a head portion 110 and a handle portion 160. The head portion 110 preferably contains, from a proximal to a distal direction, a fluid reservoir 120 to retain a fluid 122 to be administered, a body 130 that houses a prime mover 140 to draw the fluid from the reservoir 120 and propel the fluid 122 out the distal end of the device 100, and a nozzle assembly 150 which aerosolizes the fluid 122 and to form a mist pattern of the fluid 122 as the fluid 122 is directed toward its target. The handle portion 160 preferably contains the power source 170, such as a battery, an activation switch 180 to activate the device, and a system controller 190 that controls the various operational aspects of the device 100.

Head Portion

The head portion 110 includes the body 130 that connects the reservoir 120, the prime mover 140, and the nozzle assembly 150 together. The head portion 110 is connected to the handle portion 160 and provides a conduit for electrical leads (not shown) extending from the reservoir 120 and the prime mover 140 to the system controller 190.

Reservoir

Referring to FIG. 3, in which an enlarged view of a preferred embodiment of the reservoir 120 is shown, the fluid reservoir 120 may can be a vial pre-filled with the fluid 122 to be delivered to the eye. The reservoir 120 may incorporate a scale comprising a clear window 123 with volume graduation markings 124 to indicate fill level or doses of fluid 122 remaining in the reservoir 120. In the present embodiment, the scale is read with the device 100 standing on its base 166, as shown in FIG. 1.

Figure 4:
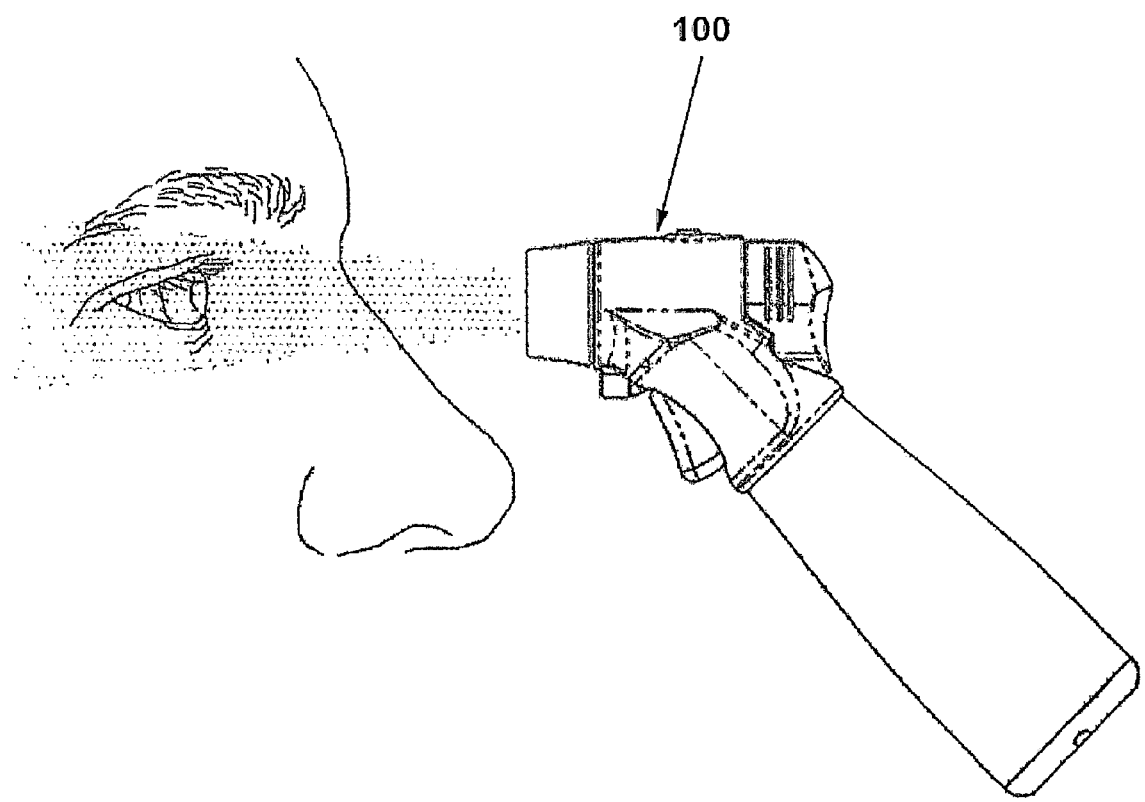
FIG. 4 is a side profile view showing the device being used to spray a mist into a patient's eye.

The reservoir 120 is preferably shaped to maintain contact with the prime mover 140 when the device 100 is held in a preferred operational orientation while spraying into an eye (as shown in FIG. 4), or is tilted in any direction within 45 degrees of horizontal. The reservoir 120 is preferably further shaped to maximize the percentage of the total fill volume that is actually dispensed.

Referring back to FIG. 3, the reservoir 120 houses the fluid 122 that is used to form the aerosolized mist when the device 100 is operated. The reservoir 120 is preferably a removable and replaceable cartridge 126 that is securely connectable to the body 130 so that the reservoir 120 does not accidentally readily separate from the body 120, yet is easily replaceable when the reservoir 120 is empty or when a reservoir 120 containing a different type of fluid is desired to be connected to the device 100.

Preferably, the reservoir 120 includes an engagement surface 128 disposed proximate to an upper and a lower side of the reservoir 120. The engagement surface 128 slides over a corresponding extension in the body 130, as shown in FIG. 3, so that the reservoir 120 is retained onto the body 130 with a frictional fit. Preferably, the extension includes a plurality of seals, such as o-rings 134, that provide a sealing engagement between the reservoir 120 and the body 130 and assists in frictionally retaining the body 120 to the reservoir 130. Alternatively, the reservoir 120 may connect with the body 130 by other means known to those skilled in the art, including, but not limited to, threaded connections, bayonet fittings, or other suitable means.

Figure 5:
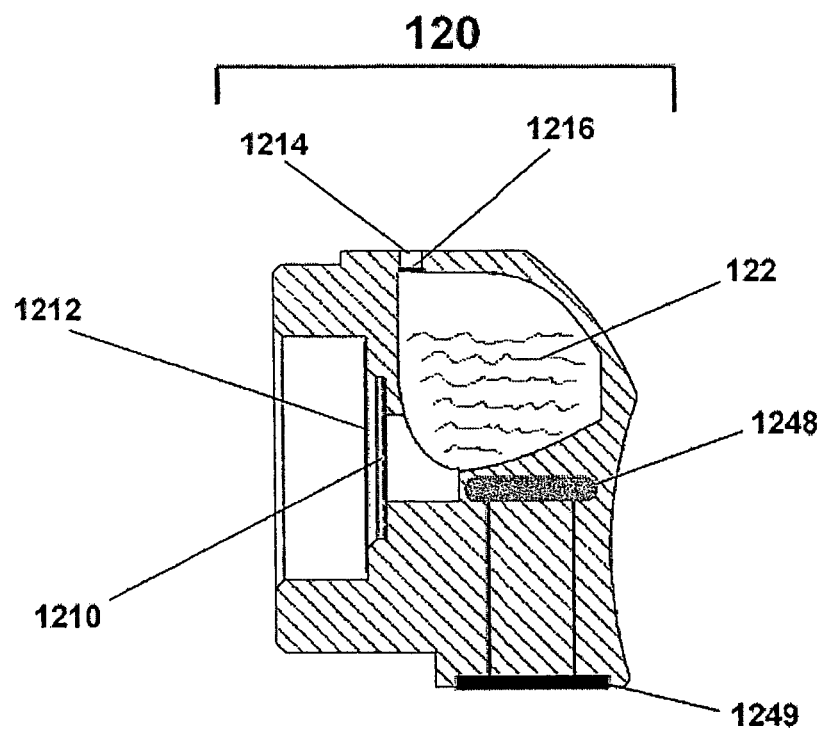

In the embodiment shown in FIG. 5, which shows the reservoir 120 removed from the remainder of the device 100, the reservoir 120 includes an open face 1210 that is covered by an air impermeable seal 1212. Initially, the open face 1210 allows the fluid 122 to be deposited into the reservoir 120, and then sealed with the seal 1212. Such a seal 1212 may be constructed from thin gauge aluminum, or some other suitable material, with a biocompatible coating disposed on both faces of the seal 1212. The seal 1212 is attached to the reservoir 120 with a biocompatible adhesive. The seal 1212 is designed to maintain sterility of the fluid 122 within the reservoir 120, yet be able to be easily punctured by the proximal end 142 of the prime mover 140 upon connecting the reservoir 120 to the body 130 so that the fluid 122 in the reservoir 120 is put into fluid communication with the proximal end 142 of the prime mover 140, as shown in FIG. 3.

For a reservoir 120 having a rigid form, such as the reservoir 120 shown in FIG. 5, a vent 1214 is formed in the wall of the reservoir 120, preferably proximate to the top of the reservoir 120, to allow air to be drawn into the reservoir 120 to compensate for the loss volume of fluid 122 as the fluid 122 is drawn out of the reservoir 120 due to operation of the device 100. A filter 1216 covers the vent 1214 to allow ambient air into the interior of the reservoir 120, but prevents fluid 122 in the reservoir 120 from leaking out of the vent 1214. While a presently preferred embodiment of the reservoir 120 envisions the fluid 122 to be prepackaged in the reservoir 120, those skilled in the art will recognize that the reservoir 120 may also be refillable, such as through the vent 1214.

Figure 6:
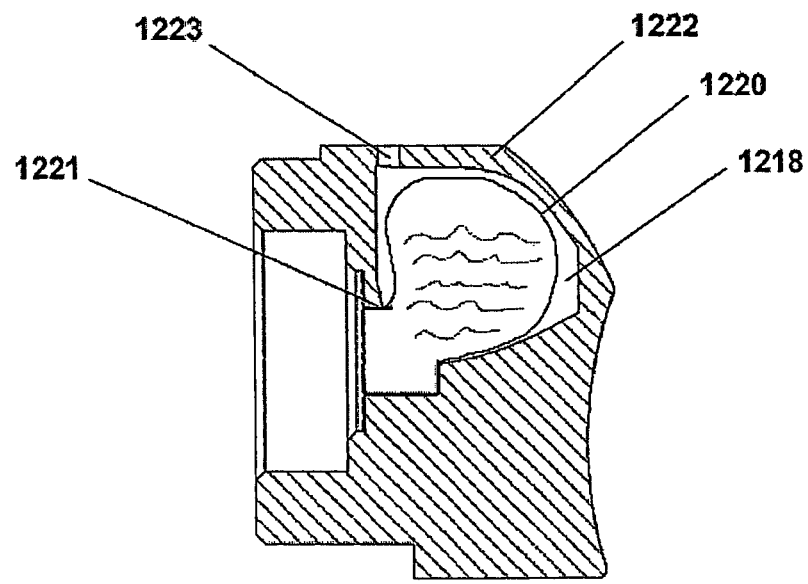

Alternatively, as shown in FIG. 6, an alternate embodiment of a reservoir 1218 may have a collapsible bladder 1220 that collapses under vacuum as the fluid 122 is drawn out of the reservoir 1218 during operation of the device 100, without any air being able to enter the reservoir 122. The bladder 1220 is preferably supple, biocompatible, and bondable. In the presently preferred embodiment, the bladder 1220 is constructed of aluminum film coated on both sides with a polymer resin. In the presently preferred embodiment, the bladder 1220 is approximately 0.025 to 0.10 mm thick. The bladder 1220 is attached to a rigid bladder neck 1221. The neck 1221 prevents the bladder 1220 from contacting the proximal end 142 of the prime mover 140 as the bladder 120 collapses. Contact with the proximal end 142 would impede the function of the prime mover 140. The bladder neck 1221 may be injection molded or extruded from a material that is rigid, biocompatible, and bondable. A material which meet these criteria includes polyethylene, although those skilled in the art will recognize that other, suitable, biocompatible materials may be used. The bladder 1220 and bladder neck 1221 are housed in a rigid reservoir housing 1222. The housing 1222 is preferably injection molded from low cost polymer resins such as PVC, ABS, or polypropylene.

An air vent 1223 in the housing 1222 allows the collapsible bladder 1220 to collapse as the fluid 122 is withdrawn from the reservoir 1218, so that no adverse suction forces are generated during operation of the device 100. The air entering the vent 1223 does not need to be filtered, since the bladder 1220 isolates the fluid 122 from the air. In this embodiment, no make-up air is required to enter the bladder 1220.

Without limiting the type of fluids that could be contained in the reservoir 120, 1218 and dispensed by the present invention, diagnostic agents used by the medical professional that could be delivered with the present invention include mydriatics/cycloplegics, anesthetics, flourescein and flourescein/ anesthetic combinations, and mydriatic reversal agents. Other agents which could be delivered with the present invention include over-the-counter agents, e.g., ophthalmic decongestants and lubricants, glaucoma medications (prestaglandins, beta blockers, alpha adrenergic agents, carbonic anhydrase inhibitors, miotics), and other ophthalmic medications. Optionally, several different therapeutic agents can be custom formulated in a single fluid to simplify adherence to multiple medication regimens.

Again, while an envisioned used for the device 100 of the present invention is directed toward ophthalmic use, those skilled in the art will recognize that the device 100 of the present invention may be used in other areas, such as respiratory treatment, and that other fluids, including respiratory medicaments, may be contained in the reservoir 120 instead.

Preferably, for photo-sensitive medicaments, the reservoir 120 may be tinted to prevent the transmission of certain deleterious wavelengths of light to the fluid 122 to prolong the useful life of the medicament in the reservoir 120. The tint may be a dark brownish tint that is presently used for such medicaments in bottle/eye dropper form.

Optionally, as shown in FIG. 2 the reservoir 120 may include a self-sealing valve 1224 in a distal wall 1226 of the reservoir 120. The self-sealing valve 1224 allows the reservoir 120 to be inserted into the body 130, and then removed from the body 130 without leaking fluid 122 from the reservoir 120.

The self-sealing valve 1224 is preferably biased toward a closed position, such as by a helical spring (not shown). A seal, such as an o-ring 1228, seals the valve 1224 against the wall 1226 of the reservoir 120 to eliminate fluid leakage from the reservoir 120 when the valve 1224 is in the closed position. A valve stem 1230 extends distally from the valve 1224. When the reservoir 120 is inserted into the body 130, the proximal end 142 of the prime mover 140 engages the valve stem 1230 and forces the valve stem 1230 into the reservoir 120, opening the reservoir 120 into fluid communication with the prime mover 140.

An alternative embodiment of a reservoir 1236 is shown in FIGS. 7 and 8. The reservoir 1236 is housed in a removable and replaceable cartridge 1237. The reservoir 1236 incorporates a generally coiled tube 1238 that is sized to partially surround the proximal end 142 of the prime mover 140. The tube 1238 may be constructed from polyethylene, although those skilled in the art will recognize that other suitable, biocompatible materials may be used. The tube 1238 preferably has a wall thickness in the range of approximately 0.1 to 0.3 mm thick, and an inside diameter in the range of approximately 1 to 5 mm. One end 1240 of the tube 1238 is fitted with a filter 1242 to allow makeup air to enter as the fluid 122 in the reservoir 1236 is drawn down. This filter 1242 is a biocompatible, gas-permeable membrane that is impermeable to liquid but permeable to air. One such material that may be used for the filter 1242 is Tyvek®. A distal end 1243 of the tube 1238 is sealed with a fluid impermeable seal 1244 that is broken by the distal end 142 of the prime mover 140 when the reservoir 1236 is connected to the device 100, as shown in FIG. 7.

As the device 100 is operated and medication is consumed, the fluid 122 is drawn along the tube 1238. The diameter of the tube 1238 is preferably specified in relation to the viscosity of the fluid 122 to insure that surface tension causes the fluid 122 to move in a column along the tube 1238, i.e., no air is drawn in by the prime mover 140 until the fluid 122 is consumed. This design has the advantage of using nearly 100% of the medication loaded into the tube 1238. This configuration has the further advantage of allowing the device 100 to operate in any orientation, even in zero gravity environments. Referring to FIG. 7, a clear window 1245 and a numerical scale 1246 on the side of the cartridge 1237 may indicate how many doses remain in the reservoir 1236. The scale 1246 may be read with the device 100 in any orientation.

While a design of a reservoir 120 with a collapsible bladder 1220 and a design of a reservoir 1236 with a coiled tube 1238 are shown, those skilled in the art will recognize that other designs of reservoirs may be used.

Optionally, as shown in FIG. 5, a heater 1248 may be incorporated into the reservoir 120 to heat the fluid 122. The heater 1248 is preferably either an inductance or a resistive heater that is electrically connected to a contact 1249 in the wall of the reservoir 120 that is electrically connectable to a contact (not shown) in the body 130 to provide electrical power to the heater 1248 to heat the fluid 122 in the reservoir 120. However, for many ophthalmic medicines, heating the medicine is not desired, and those skilled in the art will recognize that the heater 1248 may be omitted in its entirety.

Also optionally, a low level sensor 1250, shown in FIG. 3, may be incorporated into the reservoir 120 to indicate when the fluid 122 in the reservoir 120 is almost depleted. The sensor 1250 is electronically connected to the system controller 190 via electrical connection 1252 to provide an indication of fluid level in the reservoir 120. The sensor 1250 may be electronically connected to an alarm, such as an optical or aural indicator, such as a blinking light or an audible alarm.

Body

Referring back to FIG. 2, the body 130 houses the prime mover 140 and provides a connection for the fluid reservoir 120 and for the nozzle assembly 150 to engage the prime mover 140. The body 130 includes, at the distal end of the body 130, a bushing 131 that is securely bonded to the body 130, such as by an adhesive or a snap-fit. The bushing 131 includes at least one, an preferably, a plurality of bayonet clips 131*a* that are adapted to snap into the nozzle assembly 150 to retain the nozzle assembly 150 onto the body 130.

The body 130 preferably includes a connection device, such as an orifice 132, for attaching to the handle portion 160. However, those skilled in the art will recognize that other connection methods, such as snap fit, bayonet clips, or other suitable mechanisms known to those skilled in the art may be used. Preferably, the body 130 connects to the top 162 of the handle portion 160 in only a single orientation so that electrical contacts in each of the body 130 and the handle portion 160 properly engage each other when the head portion 110 is connected to the handle portion 160.

The body 130 also includes, at the proximal end of the body 130, a collar spacer 133 that is fixedly connected to the body 130 to provide optimum spacing of the proximal end 142 of the prime mover 140 within the reservoir 120 to optimize the ability of the prime mover 140 to withdraw the fluid 122 from the reservoir 120 during operation of the device 100.

The body 130 houses the prime mover 140, and provides connection means for the reservoir 120, the nozzle assembly 150, and the handle portion 160. The retainer 135 is fixedly connected to the body 130 and also releasably retains the reservoir 120 so that the reservoir 120 is removable from the remainder of the device 100. As described above, the retainer 135 may include an engagement surface, or alternatively, other connection means, such as threaded connections, or other means known to those skilled in the art.

The body 130 includes a generally tubular passage 136 that is sized to accept the proximal end 142 of the prime mover 140. A spacer recess 137 is disposed at the distal end of the body 130, preferably below the passage 136. The spacer recess 137 is used to releasably retain a targeting means, which will be described in detail later herein.

A seal 138 is disposed about the proximal end of the passage 136. The seal 138 prevents any fluid 122 from leaking out of the reservoir 120 when the reservoir 120 is attached to the body 130. In the present embodiment, the seal 138 is formed in the shape of a ring by injection molding or liquid injection molding using medical grade silicones or urethanes with durometers in the range of 5 to 30 Shore A.

Preferably, the body 130 includes an activation indicator 1310 that is disposed on the top of the body 130. The activation indicator 1310 may be a light, such as an LED, that provides constant illumination as long as the activation switch 180 is depressed; a light that provides blinking illumination; a sound that provides audible indication, either by constant or by periodic beeping; some combination of these listed indicators, or some other indication that would indicate to the user that the device is ready for operation. The activation indicator 1310 operates when the activation switch 180 is initially depressed by the user. The activation indicator 1310 alerts the user that the device 100 is "ON" and is about to spray the fluid 122 from the nozzle assembly 150. The activation indicator 1310 is electronically connected to the system controller 190 via electrical leads (not shown).

The body 130 may be machined from solid metal or plastic stock, or may be injection molded with polymer resins such as ABS, styrene, PVC, or other suitable material, as will be recognized by those skilled in the art. The body 130 may be injection molded or manufactured by other methods known by those skilled in the art. Preferably, the body 130 has a durometer within the range of approximately 90 to 100 Shore A.

Prime Mover

Figure 9:
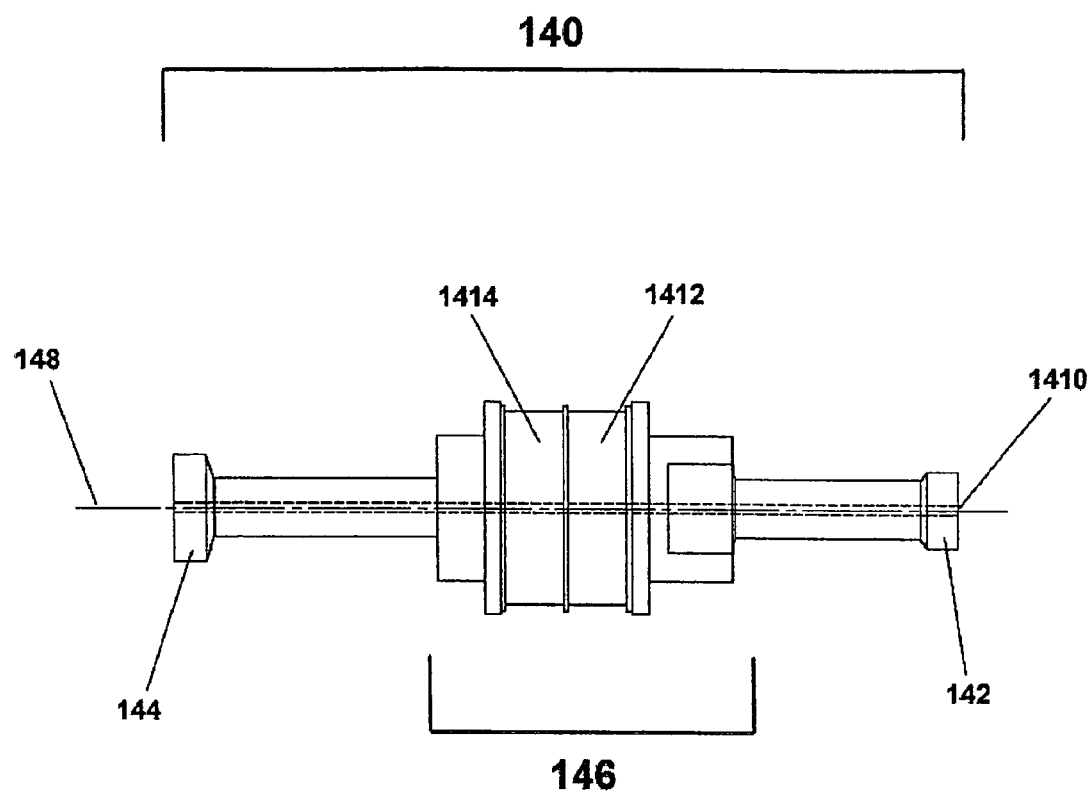
Figure 10:
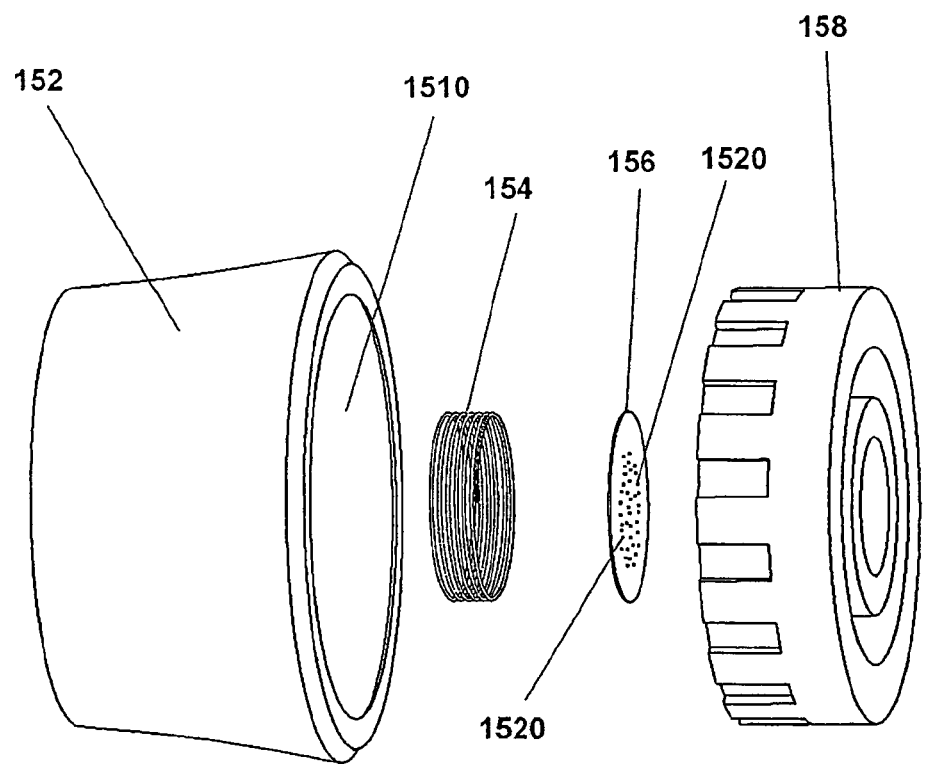
Figure 11:
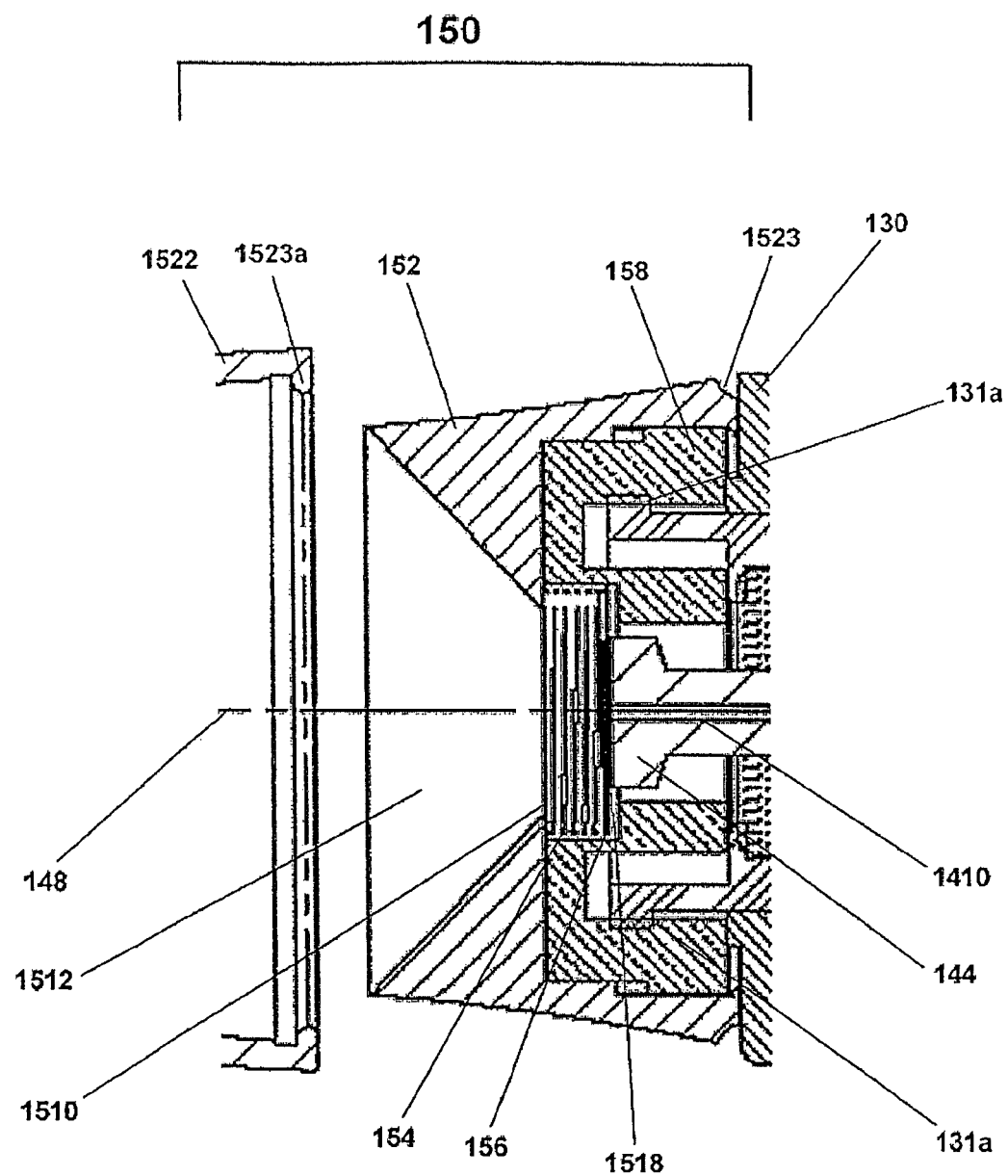
Figure 12A:
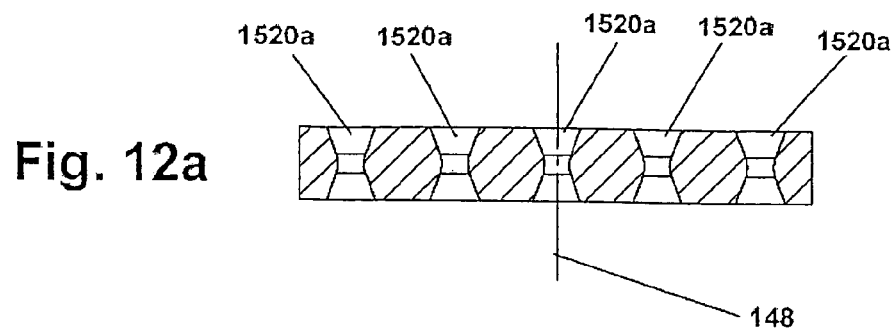
Figure 12B:
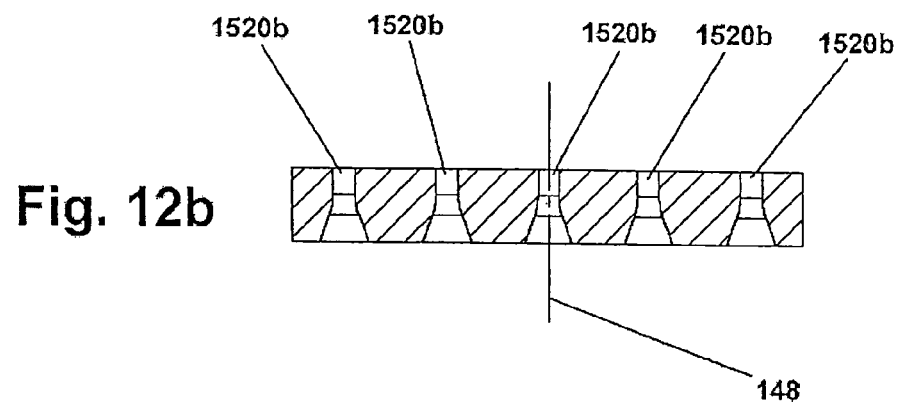
Figure 12C:
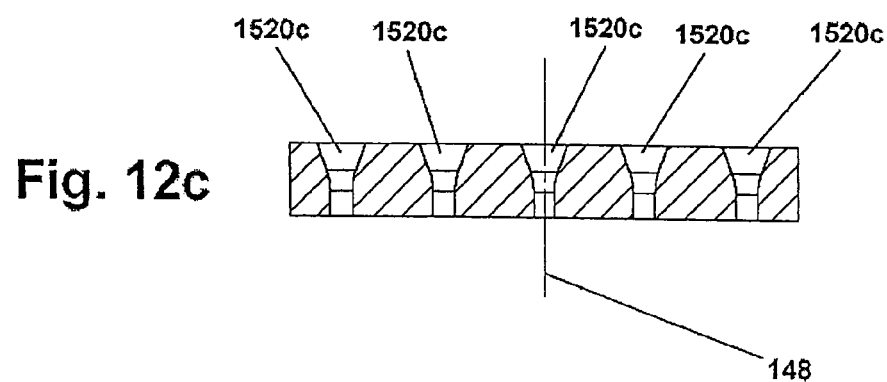
Figure 12D:
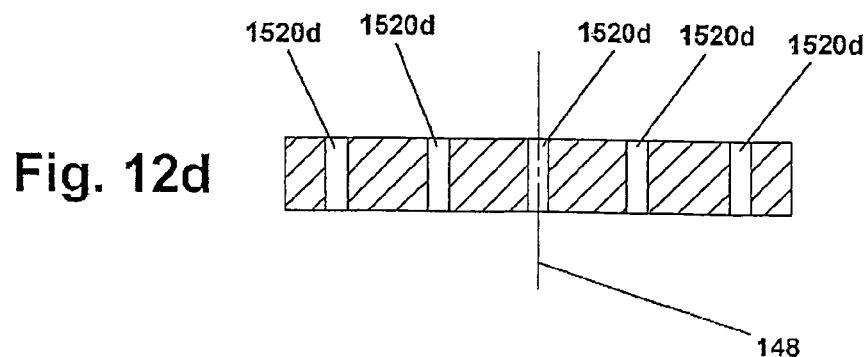
Figure 14:
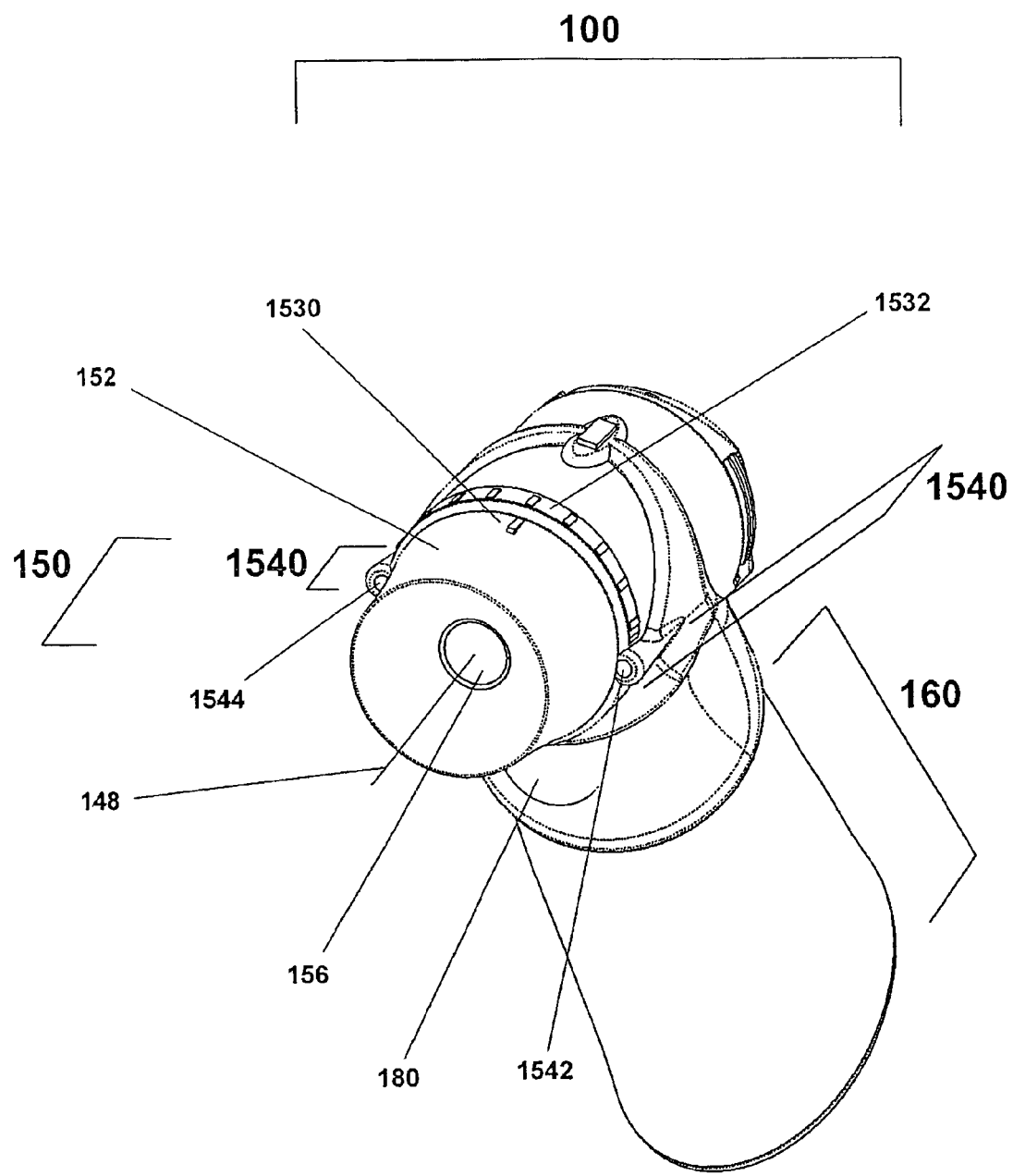

Referring still to FIG. 2, as well as to FIG. 9, the prime mover 140 will now be described. The prime mover 140 is shown in FIG. 2 in relation to the nozzle assembly 150 and the reservoir 120. The prime mover 140 is preferably an ultrasonic oscillator formed by a piezoelectric assembly such as that found in the Omron Micro-Air model NE-U03. The NE-U03 is a commercially available nebulizer that is typically used in nebulizers for bronchial therapy. However, the inventors of the present invention have discovered that this particular nebulizer is also suited for delivery of ophthalmic medicine to satisfy the needs that the present invention is intended to satisfy. The preferred piezoelectric assembly is described in detail in U.S. Pat. No. 6,651,650, the disclosure of which is incorporated herein by reference. However, those skilled in the art will recognize that the NE-U03 may be substituted for other piezoelectric assemblies, such as those discussed in the article *Nebulizers that Use a Vibrating Mesh or Plate with Multiple Aperatures to Generate Aerosol*, by Rajiv Dhand MD, Respiratory Care, December 2002, Vol. 47, No. 12, which is also incorporated by reference herein. Alternatively, instead of using piezoelectric assemblies, those skilled in the art will recognize that other prime movers that are not piezoelectrically operated may be used. Examples of such other suitable prime movers include electric pumps, manual pumps, compressed gas, or other suitable prime movers, as will be recognized by those skilled in the art.

The prime mover 140 includes a proximal end 142, a distal end 144, and a central portion 146 disposed between the proximal end 142 and the distal end 144. A longitudinal axis 148 extends along a length of the prime mover 140 between the proximal end 142 and the distal end 144. A longitudinally extending lumen 1410 extends along the longitudinal axis 148 and extends the length of the prime mover 140. Preferably, a perpendicular cross section of the lumen 1410 is generally circular in shape and has a diameter of approximately between 0.25 and 1.0 mm. However, those skilled in the art will recognize that the lumen 1410 may have other cross sectional shapes, such as a generally oblong, oval, or elongated shape.

The central portion 146 includes at least two generally annular piezoelectric elements 1412, 1414 that surround the lumen 1410. The piezoelectric elements 1412, 1414 are electrically connected to the power source 170, which drives the piezoelectric elements 1412, 1414 during operation of the device 100.

Referring to FIG. 2, the prime mover 140 is retained within the body 130 by a distal seal 1426. The distal seal 1426 is generally annular in shape and taper from a wider diameter to a smaller diameter from the piezoelectric elements 1412, 1414 toward the proximal end 142 and the distal end 144, respectively. The distal seal 1426, along with the seal 138, restricts movement of the prime mover 140 within the body 130 and prevent fluid 122 that may leak through the device 100 from engaging the central portion 146 of the prime mover 140. Preferably, the seal 1426 is constructed from a biocompatible material, such as medical grade silicon or urethane, although those skilled in the art will recognize that other suitable material may be used.

Referring back to FIG. 3, the proximal end 142 is immersed in the fluid 122 in the reservoir 120. When the piezoelectric elements 1412, 1414 are excited, such as during operation of the device 100, standing waves are formed which draw the fluid 122 into the proximal end 142 of the prime mover 140 and along the lumen 1410. The standing waves propel the fluid 122 along the lumen 1410 to the distal end 144 of the prime mover 140 and to the nozzle assembly 150, which is in mechanical contact with the distal end 144 of the prime mover 140. As the prime mover 140 vibrates at ultrasonic frequencies, the prime mover 140 transfers a portion of its vibrational power to a mesh plate 156 in the nozzle assembly 150, as will be described in more detail later herein. The fluid 122 that has been propelled along the lumen 1410 contacts the mesh plate 156. The vibration of the plate 156 aerosolizes the fluid 122 and accelerates the fluid 122 away from the device 100 and toward the patient.

Nozzle Assembly

The nozzle assembly 150 is shown in an exploded perspective view in FIG. 10, as well as in an elevated sectional view in FIG. 11. The nozzle assembly 150 forms the mist that is discharged from the device 100 during operation. The nozzle assembly 150 includes, from a distal to a proximal direction, a cap 152, a biasing member 154, a mesh plate 156, and a retainer 158.

The cap 152 is generally annular, with a central opening 1510 disposed along the longitudinal axis 148. Preferably, the body of the cap 152 extends in a distal direction and generally away from the longitudinal axis 148 to form a concave volume 1512 distal of the central opening 1510. The concave volume 1512 reduces the likelihood that a foreign object, such as a user's finger, will touch the mesh plate 156, potentially contaminating the plate 156.

The cap 152 preferably includes a releasable lock feature, such as a female threaded connection (not shown) that releasably threadingly engages the retainer 158, which has a mating twist lock feature, such as a mating male threaded connection (not shown). However, those skilled in the art will recognize that the cap 152 may engage with the retainer 158 by other means not shown, such as by snap engagement, bayonet means, or other suitable means known to those skilled in the art.

The mesh plate 156 is biased against the distal end 144 of the prime mover 140 by the biasing element 154, such as a helical spring, that is disposed between the cap 152 and the mesh plate 156. The biasing element 154 ensures that the mesh plate 156 is firmly engaged with the distal end 144 of the prime mover 140 to provide proper dispersion of the fluid 122 through the mesh plate 156 during operation of the device 100. While a helical spring is preferred as the biasing element 154 because a helical spring provides a generally uniform biasing force around its perimeter, those skilled in the art will recognize that other types of biasing elements, such a leaf springs, may be used instead. As shown in FIG. 11, a clearance space 1518 is formed between the proximal side of the mesh plate 156 and the retainer 158 to allow the mesh plate 156 to vibrate during operation.

The mesh plate 156 is formed of a rigid material that is biocompatible and non-oxidizing, such as alumina ceramics, titanium allows, or stainless steel alloys. As shown in FIG. 10, an array of openings 1520 is formed in the mesh plate 156. The number, density, size, and shape of the openings 1520 contribute to determining mist parameters such as volume, velocity, and droplet size distribution. The openings 1520 may be drilled by mechanical means, by fine jets of water, or by lasers. The preferred embodiment of the mesh plate 156 is constructed from a ceramic material and measures approximately 9 mm in diameter and 0.1 mm thick, having between 500 and 5000 openings 1520 drilled by laser. The openings 1520 preferably have diameters in the range of approximately 0.5 to 30 microns. A mask (not shown) may be used that enables many openings 1520 to be drilled simultaneously. After each group of openings 1520 is drilled, the mask or the mesh plate 156 is indexed to a new position and the next set of openings 1520 is drilled. This step-and-repeat process continues until all the openings 1520 are made.

Enlarged cross sections of several embodiments of openings 1520*a*, 1520*b*, 1520*c*, 1520*d*, and 1520*e* in mesh plates 156*a*, 156*b*, 156*c*, 156*d*, 156*e* are shown in FIGS. 12*a*, 12*b*, 12*c*, 12*d*, 12*e*. Referring to FIG. 12*a*, the mesh openings 1520*a* in the mesh plate 156*a* are preferably circular in cross section along a plane parallel to the longitudinal axis 148, with an approximate hourglass cross section along a plane perpendicular to the longitudinal axis 148. Referring to FIG. 12*b*, the mesh openings 1520*b* in the mesh plate 156*b* are wider at the proximal (bottom) end of the plate 156*b* and narrower at the distal (top) end of the plate 156*b*. Referring to FIG. 12*c*, the mesh openings 1520*c* in the mesh plate 156*c* are narrower at the proximal (bottom) end of the plate 156*c* and wider at the distal (top) end of the plate 156c. Referring to FIG. 12d, the mesh openings 1520d in the mesh plate 156d have a generally constant diameter between the proximal (bottom) end of the plate 156d and the distal (top) end of the plate 156d.

The mesh plate may 156 incorporate one of several designs of openings 1520 as shown in FIGS. 13a through 13e. In the top plan view of the design shown in FIG. 13a, a mesh plate 156e is generally planar, with a plurality of openings 1520 in a generally circular pattern, with a center of the generally circular pattern along the longitudinal axis 148. In the top plan view of the design shown in FIG. 12b, a mesh plate 156f is generally planar, with a plurality of openings 1520 in a generally elongated pattern, such as a rectangle or an oval. Alternatively, a mesh plate 156g may be generally convex, as shown in the side sectional view of the mesh plate 156g in FIG. 13c, to disperse the fluid 122 at a relatively wide angle to increase the field of dispersion of the fluid 122. In yet another alternative, a mesh plate 156h may be concave, as shown in the side sectional view in FIG. 13d, to disperse the fluid 122 in a relatively small area. For each of the mesh plates 156g, 156h in FIGS. 13c and 13d, the pattern of openings may be circular, as shown in FIG. 13a, or elongated, as shown in FIG. 13b. The pattern of openings is aligned with the central opening 1510 in the cap 152 so that the fluid 122 that is dispersed through the mesh plate 156 passes through the central opening 1510 and forms a mist for deposition into the eye of the patient.

In an alternate embodiment, shown in FIG. 13e, a mesh plate 156i includes a generally flat plate with openings 1520i that are angled toward the longitudinal axis 148. This design provides the benefits of an easy to produce mesh plate that directs the fluid to a focused point.

Figure 16:
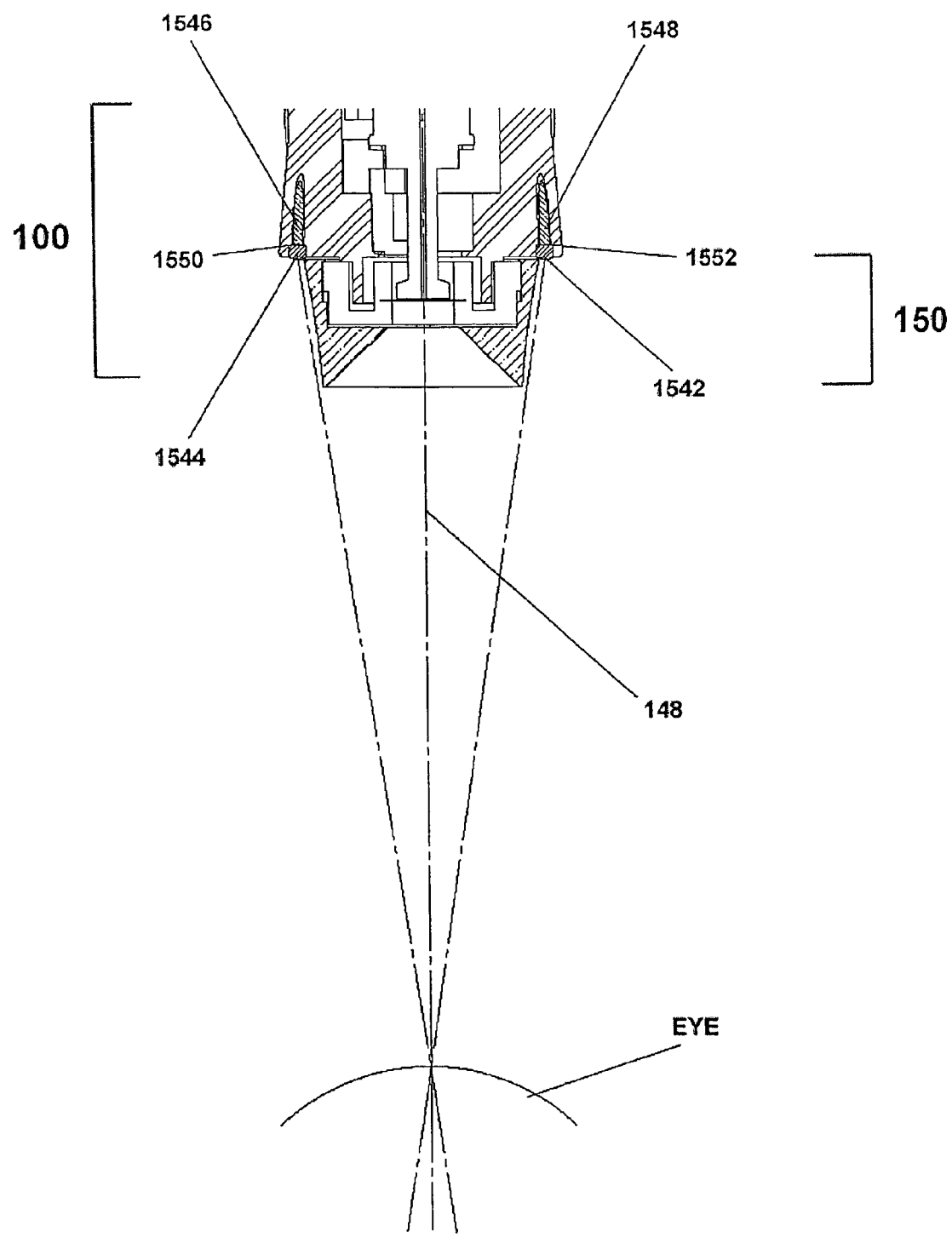
Figure 17A:
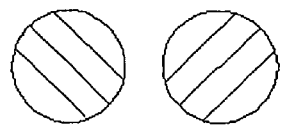
Figure 17B:
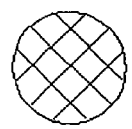
Figure 17C:
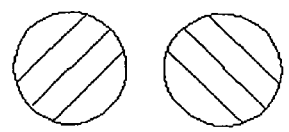

It is preferred that the openings 1520 in the mesh plate 156 generates mist particle sizes in the average range of between approximately 0.5 and 10 microns in diameter. It is also desired that the mist generated through the nozzle assembly 150 preferably extends about 100. The targeting mechanism 1540 includes two projection lenses 1542, 1544 that are disposed on the nozzle assembly 150, preferably spaced 180 degrees from each other on either side of the longitudinal axis 148. The lenses 1542, 1544 are angled toward the longitudinal axis 148 such that projections from the lenses 1542, 1544 intersect at the longitudinal axis 148 at an optimum distance for spacing the nozzle assembly 150 from the patient's eye, as shown in FIG. 16. A light source 1546, 1548 is disposed proximal of each lens 1542, 1544, respectively, with each light source 1546, 1548 being directed along the projection line of each respective lens 1542, 1544. The light sources 1546, 1548 may be LEDs, incandescent sources, lasers, or other suitable light source, as will be recognized by those skilled in the art. The light sources 1546, 1548 are electrically connected to the activation switch 180 so that the light sources 1546, 1548 activate upon initial engagement of the activation switch 180.

Preferably, the light sources 1546, 1548 and the lenses 1542, 1544 form a pattern on the target eye when the device 100 is aimed at the eye and the activation switch 180 is depressed. The pattern may be formed by separate masks 1550, 1552 that are disposed between each light source 1546, 1548 and its respective lens 1542, 1544, as shown in FIG. 16, or, alternatively, the mask may be formed on each lens 1542, 544 (not shown). In either embodiment, the targeting mechanism 1540 forms one of three general patterns on the iris or the sclera of the eye. When the device 100 is too far from the eye, a pattern similar to a pattern formed in one of FIGS. 17a, 18a, 19a, 20a, 21a is formed. When the device 100 is a correct distance from the eye, a pattern similar to the pattern formed in one of FIGS. 17b, 18b, 19b, 20b, 21b is formed. When the device 100 is too close to the eye, a pattern similar to the pattern formed in one of FIGS. 17c, 18c, 19c, 20c, 21c is formed. Those skilled in the art will recognize that the patterns shown in FIGS. 17a-21c are exemplary only, and that numerous other patterns may be formed.

In addition to assisting in determining the optimum distance for spacing the device 100 from the eye, the targeting mechanism 1540 also aids in accurately aiming the device 100 at the eye, so that the mist generated by the device 100 is directed toward the middle of the eye, and not off to the side.

While the targeting mechanism 1540 described above is useful for a professional practitioner to use to aim the device 100 at a patient, those skilled in the art will recognize that an alternative embodiment of a targeting mechanism (not shown) may be used to by a patient on himself/herself by directing the targeting mechanism onto his/her retina.

Handle Portion

Figure 15A:
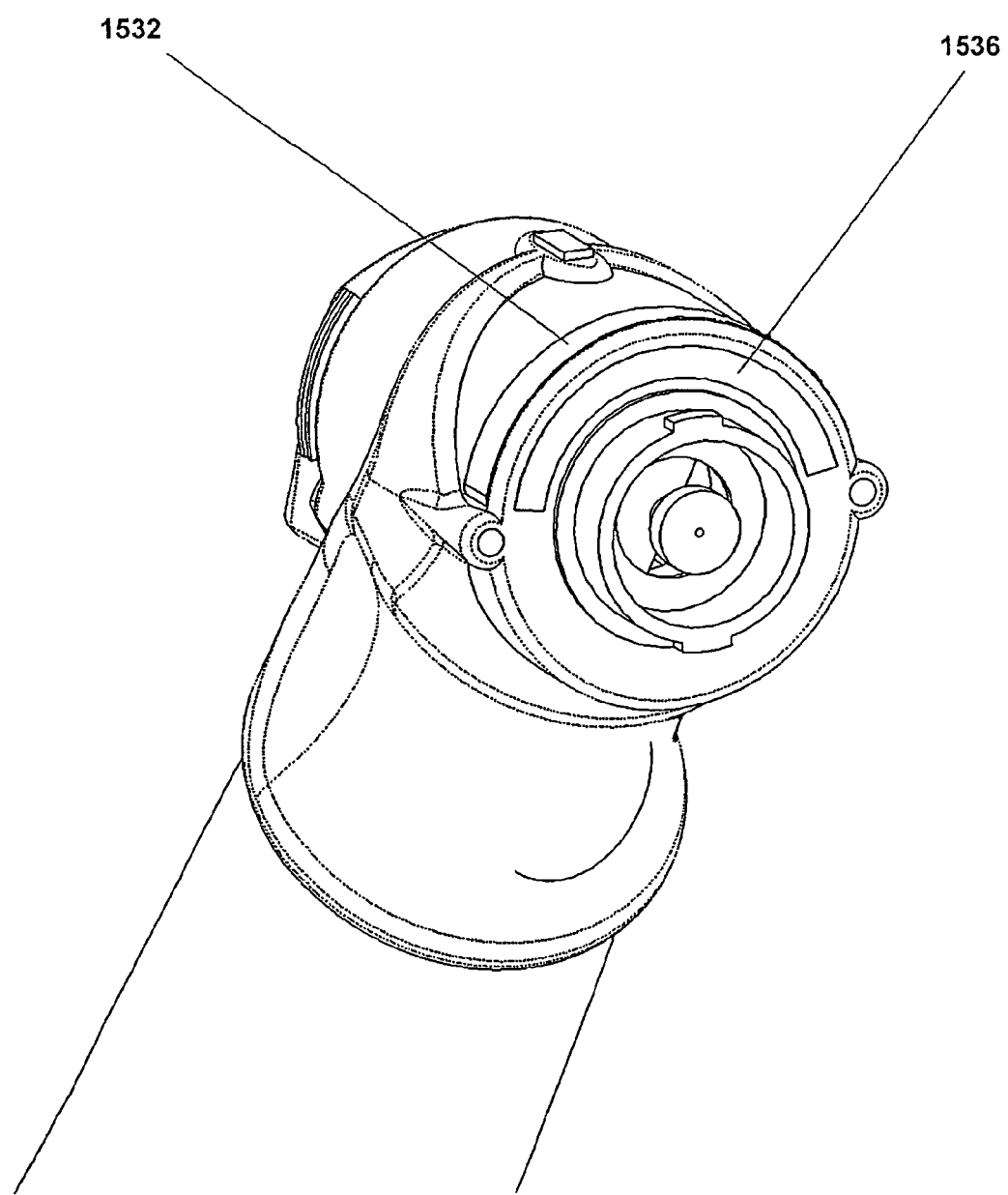
Figure 15B:
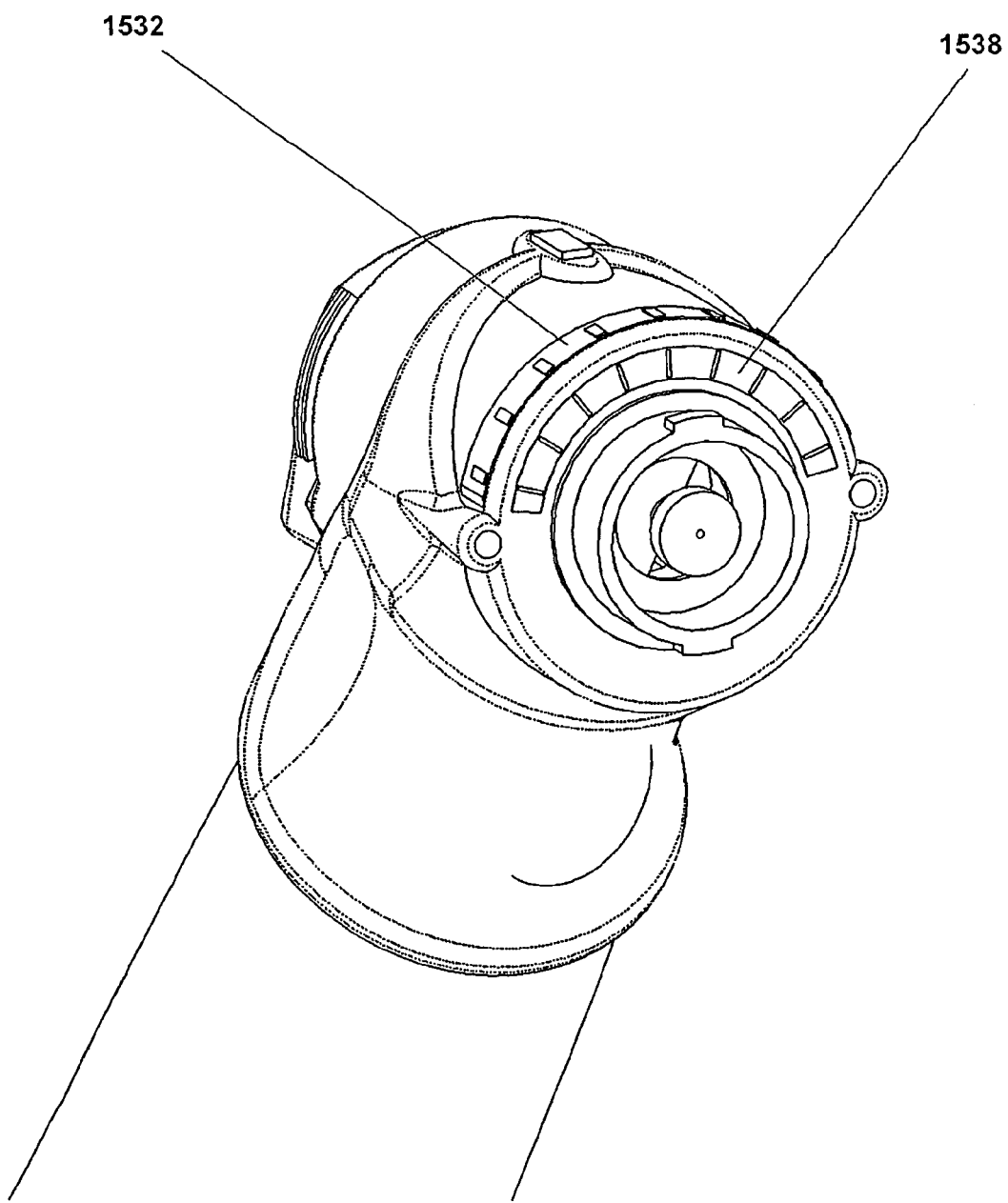
Figure 15C:
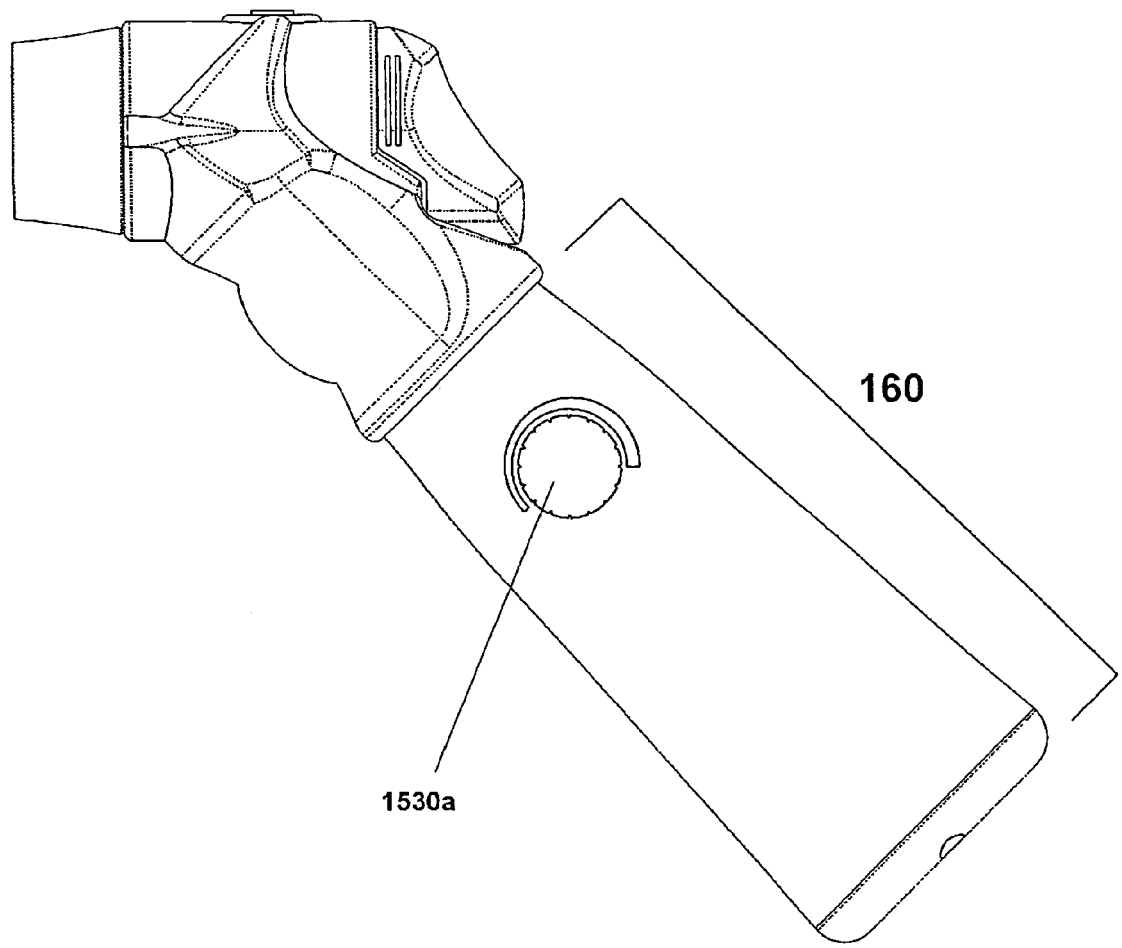

Referring back to FIGS. 1 and 2, the handle portion 160 contains the bulk of the electronics, as well as the activation switch 180 and the power supply 170. As described previously above, the handle portion 160 may also include a dosage adjuster 1530a (shown in FIG. 15c) for adjusting the amount of fluid 122 that is discharged per use. The handle portion 160 includes an elongated body 162 having a top end 164, which is connected to the body portion 130, as well as a bottom end 165, which is configured for removable insertion into a base 166.

In a non-use operation, the device 100 is preferably disposed in the base 166, as shown in FIGS. 1 and 2. The base 166 typically rests on a desktop and holds the device 100 such that the device 100 can simply be lifted from the receiver for use. The base 166 includes a cavity 167 that is sized and shaped to securely receive the bottom end 165 of the handle portion 160. The base 166 may also be weighted to keep the device 100 from toppling over after the device 100 is inserted into the base 166. Alternately, the base 166 may include an adhesion device, such as a suction cup or an adhesive (not shown), to keep the device 100 from toppling over.

Preferably, the handle portion 160 and the base 166 may be separately machined from solid metal or plastic stock, or may be injection molded with impact resistant polymer resins, such as ABS, polycarbonate, PVC, or other suitable material, as will be recognized by those skilled in the art. The handle portion 160 may optionally include a rubberized grip 168, at least along a length of the handle portion 160 facing the distal end of the device 100. The rubberized grip 168 is softer for the user and helps prevent the user from accidentally dropping the device 100. The grip 168 may also include indentations for a user's fingers to enhance ergonomics. The grip 168 may be manufactured from a material having a hardness in the range of 10-50 Shore A that may be molded separately and bonded onto the handle portion 160.

Referring now to FIGS. 22a and 22b, an optional mechanical targeting means 1620, for setting an optimum distance between the nozzle assembly 150 and the patient's eye, is shown. In lieu of the electronic targeting means 1540 shown and described with respect to FIGS. 14 and 17a-21c, the targeting means 1620 may be mechanically incorporated into the device 100.

The targeting means 1620 includes a generally elongated member 1622 that includes a connected end 1624 that is releasably inserted into the spacer recess 137, and a free end 1628 that is disposed away from the connected end 1624. As shown in FIG. 22b, the free end 1628 is generally "Tee-shaped" and is preferably formed in the shape of an eyelid depressor to depress the tear sac under the eye and to provide a larger ocular surface area for contact with the fluid 122 being dispensed from the device 100. Since the free end 1628 engages the patient and the patient's eye area, it is preferred that the targeting means 1620 is disposable between uses to avoid any contamination from one patient to the next.

Preferably, the elongated member 1622 is constructed from impact resistant polymer resins, such as ABS, polycarbonate, PVC, or some other suitable rigid material to minimize deflection of the elongated member 1622 during operation. Also preferably, the free end 1628 is either coated with or constructed from a soft material, such as rubber in order to reduce the likelihood of eye injury in the event that the free end 1628 accidentally engages the eye.

Power

A preferred power source 170 for the device 100 is battery power. As can be seen in FIGS. 1 and 2, a battery 172 is removably inserted into the bottom end 165 of the handle portion 160. A cover 169 retains the battery 172 in the handle portion 160. The cover 169 is removable so that the battery 172 may be easily replaced. The cover 169 may be releasably connected to the handle portion 160 by clips, threaded fasteners, or other means known to those skilled in the art.

The battery 172 may be a single-use lithium ion or alkaline type, or the battery 172 may be rechargeable lithium-ion, nickel-cadmium, nickel-metal-hydride, or other battery type. The battery 172 may be a single battery or a plurality of batteries electrically connected in series. For example, two lithium photo batteries NEDA/ANSI type CR2 (e.g. Duracell Ultra CR2 Li/MnO2) may be connected in series will be used to power the device 100. The batteries 172 are preferably rated for 3V and approximately 2000 mAh. The batteries 172 are connected in series to provide a total capacity 2000 mAh at 6V. The batteries 172 preferably have a peak current rating of at least 1.8 A.

If a rechargeable battery is used, a charger is required. Those skilled in the art will recognize that the charger may be integrated into the device 100 or enclosed in a separate enclosure, such as in the base 166. The base 166 includes a standard 110V electrical cable 1610 extending therefrom that is electrically connected to an AC/DC converter (not shown) in the base 166 that converts 110V AC supply to 6V DC. The base 166 also includes a pair of contacts (not shown) that engage recharger contacts (not shown) in the bottom end 165 of the handle portion 160 when the device 100 is inserted into the base 166.

Alternatively, the device 100 may be designed such that the battery 172 can be easily removed from the device 100 and charged in a separate charger (not shown). A further alternative is to replace the battery with an AC-to-DC converter, and power the device 100 through a line cord connected to an AC source.

Activation Switch

An activation switch 180 extends through the handle portion 160 to activate the device 100 upon a user engaging the activation switch 180. The activation switch 180 is preferably a button, as is shown in FIG. 2, or some other suitable device, such as a trigger, as will be recognized by those skilled in the art. Alternatively, the activation switch may be a foot switch (not shown) that is electronically connected to the system controller 190 to activate the device 100, such as by an electrical line.

The activation switch 180 is electronically connected to the system controller 190 via leads 182, 184. Preferably, the activation switch 180 is a three-position switch such that, when the activation switch 180 is depressed an initial amount from an open position to an initially closed position, the device 100 is activated. This activation illuminates the activation indicator 1310 to indicate that the device 100 is about to operate. When the activation switch 180 is completely depressed, the activation switch 180 transmits a signal, through the system controller 190, to operate the prime mover 140 for a period of time determined, through the system controller 190, by the settings on the dosage adjuster 1530. Preferably, the time period for operation extends between approximately 0.5 and 5 seconds. However, operation time of the prime mover 140 is not dependent on the duration of time that the activation switch 180 is depressed, but on the settings of the dosage adjuster 1530. However, it is preferred that, if the activation switch 180 is depressed for an extended period of time, such as greater than two seconds, the system controller 190 interprets the signal received from the activation switch 180 as a signal to run the device 100 continuously for a predetermined, extended period of time, such as thirty (30) seconds, such as to run a cleaning solution such as saline, through the device 100 to clean the device 100. Alternatively, if the activation switch 180 is depressed for longer than the predetermined period of time, the system controller 190 will provide power for the prime mover 140 to operate as long as the activation switch 180 is fully depressed.

Electronics

The primary function of the system controller 190 is to energize the prime mover 140, which is preferably a piezoelectric transducer assembly or other piezo device, as described above. When energized, the prime mover 140 generates a mist of fluid droplets from the fluid 122. The energizing signal for the prime mover 140 must excite the prime mover 140 at the proper resonant frequency, and must supply enough energy to the prime mover 140 to cause misting. A simple user interface, such as the activation switch 180, is required for operation and control of the prime mover 140. A microprocessor 192 will be used to provide intelligence for the interface between the activation switch 180 and the prime mover 140, and to supervise the circuits driving the prime mover 140, as well as all of the electronic features.

The system controller 190 controls operation of the device 100 and includes a microprocessor 192, preferably in the form of a PCBA (Printed Circuit Board Assembly), to incorporate the electronics for operation of the device 100. FIG. 23 shows an electronic block diagram for a preferred embodiment of the system controller 190. The microprocessor 192 is housed in the system controller 190, through which a majority of the operation of the device 100 passes. The system controller 190 preferably also contains a non-volatile memory, input/output ("I/O") devices, digital-to-analog ("D/A") and analog-to-digital ("A/D") converters, driver circuits, firmware, and other electronic components, as will be described in detail herein. Alternatively, those skilled in the art will recognize that simple logic components may be used.

The activation switch 180 is part of a normally open ("NO") circuit that includes the activation indicator 1310. As described above, the activation switch 180 is a three-position switch, with the first position in the NO condition. The second position, when the activation switch 180 is depressed part way, powers the activation indicator 1310 to indicate to the user that the device 100 is on. The third position, when the activation switch 180 is fully depressed, activates the device 100 to operate the prime mover 140 to generate a mist from the nozzle assembly 150 for medication dispensing to the patient. To conserve power and lengthen operational battery life, all circuits are disconnected from power while the activation switch 180 is open.

A power management & low battery indicator 194 includes an electronic circuit that automatically measures the battery voltage and provides a visual or audible (beeping) indication if the voltage has dropped below a preset level. Power management chips (also known as "gas gages") are commercially available for various battery types, or such a circuit may be constructed from discrete components. Preferably, the circuit also provides "sleep" or "hibernate" modes, as are known to those skilled in the art, in which battery life is extended by reducing power consumption when the device 100 has been inactive for a preset amount of time.

An optional power conditioning circuit 196 provides a constant and regulated voltage to the rest of the system controller 190. Power conditioning chips are commercially available for various voltage and current requirements, or alternatively, such a circuit may be constructed from discrete components.

A voltage step-up & driver (VSD) circuit 198 powers the prime mover 140. For a prime mover 140 that includes the piezo device described above, the purpose of the VSD circuit 198 is to drive the piezoelectric crystal contained in the piezo device at a desired resonant frequency. Different crystals and piezoelectric assemblies have different resonant frequencies, as well as different Q-factors, so the VSD circuit 198 is preferably custom designed to match the operating characteristics of the particular piezo device. The VSD circuit 198 contains an oscillator formed of integrated and/or discrete components such as power transistors, power diodes, capacitors, and coils.

Preferably, the piezo device is driven by a square wave at its resonant frequency in the range of 50 KHz to 70 KHz. Since each piezo device has a slightly different resonant frequency, the circuit will use a Phase Lock Loop (PLL) or other feedback technique with a Voltage Controlled Oscillator (VCO) to lock on to the piezo resonant frequency and to automatically adjust the drive signal frequency as the resonant frequency varies. The piezo device is preferably driven by a peak-to-peak signal in the range of 200V, or as appropriate to provide sufficient misting. Using the preferred Omron piezoelectric device described above, the mist volume produced with this method is in the range of approximately 10 to 100 microliters/second.

The system controller 190 also optionally includes a heater control 1910 and that is electronically connected to the optional reservoir heater 1248 to heat the fluid 122 in the reservoir 120, as desired. The heater control 1910 includes a feedback loop to control the desired temperature of the fluid 122 in the reservoir 120. A heater power supply 1912 is also electronically connected to the system controller 190 to provide a power supply to the optional heater 1248.

Low Fluid Level

If the device 100 includes the low level sensor 1250 in the reservoir 120 as described above, the device 100 also includes a low fluid level alarm 1914 that is set to alarm when the fluid 122 in the reservoir 120 is depleted to a predetermined level. The low reservoir sensor 1250 is programmed to transmit a signal to the system controller 190 when the fluid level reaches the predetermined level. The system controller 190 in turn transmits a signal to the alarm 1914. The alarm 1914 may be a visual alarm, such as a blinking light, or the alarm 1914 may be an audible alarm, such as a beep.

Dosage Adjustment

A manual method and apparatus for adjusting dosage amount dispensed during operation of the device 100, using the dosage adjuster 1530, 1530a has been previously described. Adjustment of the dosage adjuster 1530, 1530a transmits a signal to a dose control circuit 1916 to determine the length of time that the prime mover 140 operates to dispense the fluid 122 from the reservoir 120 to the patient. The system controller 190 also includes a flow volume control circuit 1918 that determines the volume of the fluid 122 per unit time that is dispensed through the prime mover 140. The total amount of the fluid 122 dispensed is determined by the value of the flow rate as determined by the flow volume control circuit 1918 times the length of time of operation of the prime mover 140 as determined by the dose control circuit 1916. Preferably, the flow volume control circuit 1918 is preprogrammed into the system controller 190, while the dose control circuit 1916 may be manually adjusted based on the type of medication and the dosage that the prescribing physician determines is necessary based on the patient's condition.

Alternatively, instead of manually adjusting the dosage amount, the dosage amount may be adjusted electronically, such as by external calibration of the system controller 190 to adjust operational values of the dose control circuit 1916 and the flow volume control circuit 1918 based on need.

Dosage Complete Indicator

The system controller 190 also includes a "dosage complete" indicator 1920 that indicates when the device 100 has dispensed the prescribed amount of fluid 122 from the reservoir 120. The indicator 1920 may be may be a visual alarm, such as a blinking light, or the indicator 1920 may be an audible alarm, such as a beep. The indicator 1920 preferably is activated after a slight time delay, such as approximately 0.5 second, after the device 100 ceases to dispense the fluid 122 from the nozzle assembly 150. This delay ensures that the user does not remove the device 100 from in front of the patient's eye until all of the prescribed dose of medication has been dispensed from the device 100. Since the system controller 190 controls operation of the prime move 140, the system controller 190 is able to calculate the desired delay time between stopping operation of the prime mover 140 and sending the signal to the indicator 1920 to indicate that the dosage is complete.

Targeting Optics

If the optional electronic targeting mechanism 1540 is used, depressing the activation switch 180 to the first position transmits a signal to the system controller 190 to activate the targeting mechanism 1540, illuminating the light sources 1546, 1548 to project images on the patient's eye. The targeting mechanism 1540 remains activated when the activation switch 180 is depressed to the second position. When the activation switch 180 is released, signal to the system controller 190 ceases, and the targeting mechanism 1540 is deactivated by the system controller 190.

Outside Communications

Optionally, the device 100 may include an input/output (I/O) device 1922 for transmitting information between the device 100 and an outside device, such as a personal computer, PDA, or other such electronic device that is capable of displaying information transmitted from the device 100. Information that may be transmitted from the device 100 includes, but is not limited to, usage information, such as the number of times the device 100 was used, and at what times; dosage amount per application; and current and voltage draw of the device 100 during use, as well as other operational information about the device 100. Further, information may be transmitted from the outside device to the device 100. Such information may include, but is not limited to, clearance information to clear the system controller 190 memory of previous information that has already been downloaded to the outside device; operational information that allows the device 100 to be used with particular medicament reservoirs; temperature settings for the heater control 1910; and operational duration information to adjust the dose control circuit 1916 and the flow volume control circuit 1918 to adjust dosage amounts, as well as other information that may be transmitted to the system controller 190.

As shown in FIG. 2, the 100 device 1922 may include a port 1612 on the handle portion 160 for physically connecting the device 190 to the outside device, such as by a cable. The port 1612 may be a standard Universal Serial Bus (USB) port, or some other suitable port as will be recognized by those skilled in the art. The port 1612 is electronically connected to the system controller 190 by a port cable 1614 that transmits information between the port 1612 and the system controller 190. Alternatively, the I/O device 1922 may include an infrared transmitter/receiver (not shown) that allows the device 100 to be placed near, but not physically connected to, the outside device to exchange information such as the information described above.

A pediatric version of a device 200 according to an alternate embodiment of the present invention, shown in FIG. 24, may include a facade 204 at the distal end 202 of the device 200 that encourages younger patients to look in the direction of the device 200. For example, for ophthalmic delivery, the facade 204 may include a clown face or an animal face that catches the attention of the patient and distracts the patient from the medicament that is being dispensed from the device 200. In the embodiment shown in FIG. 24, the nose of the facade is the mesh plate 156. Alternatively, the facade 204 may include moving parts to distract the patient during operation of the device 200.

Alternatively, a veterinary version of a device 300 according to yet another alternate embodiment of the present invention, shown in FIG. 25, may include a facade 304 at the distal end 302 of the device 300 that distracts the animal that is being medicated. The facade 304 may include a moving element for the animal to focus upon during administration of the medicament.

The embodiments shown and described above may be offered in a reusable configuration. In this event, the parts may be injection molding from clear polymer resins that withstand repeated sterilization by steam autoclave, such as autoclaveable versions of acrylics, styrenes, and polycarbonates.

Alternatively, the embodiments shown may be offered as a sterile disposable. In this case it may be injection molded from a wide variety of clear polymer resins, including acrylics, styrenes, urethanes, PMMA, and polycarbonates. These resins are generally compatible with industrial sterilization by e-beam, gamma, and EtO.

Use

Between uses, the device 110 is typically stored in the base 166, with the bottom end 165 of the handle portion 160 inserted into the cavity 167 in the base 166. The electrical cable 1610 is connected to an external power supply to provide electrical power to the batteries 172 to charge/recharge the batteries 172. The heater 1248, if used, heats the fluid 122 in the reservoir. The temperature of the fluid 122 is controlled by the heater controller 1910 to maintain the fluid 122 at a desired temperature.

The device 100 is designed so that it can be used by one person to self administer medicament, such as a patient in his/her home, or, the device 100 can be used by one person to administer medicament to a second person, such as a medical professional treating a patient in a medical office or a hospital setting.

For self use, the user removes the device 100 from the base 160 and aims the discharge end of the nozzle assembly 150 toward the eye into which the user intends to insert the eye medication. If the optional mechanical targeting means 1620 is connected to the device 100, the user inserts the connected end 1624 into the spacer recess 137. The user then uses the free end 1628 of the targeting means 1620 to depress the eyelid. When the device 100 is in the desired position, the user then uses his/her thumb, as shown in FIG. 26, to depress the activation switch 180. By pressing the activation switch 180 to the first position, the activation indicator 1310 is illuminated, indicating that the device 100 is ready for operation.

For professional use on a patient, the user, such as an optometrist or an ophthalmologist, removes the device 100 from the base 160 and aims the discharge end of the nozzle assembly 150 toward the eye into which the user intends to insert the eye medication. If the optional mechanical targeting means 1620 is connected to the device 100, the user inserts the connected end 1624 into the spacer recess 137. The user then uses the free end 1628 of the targeting means 1620 to depress the eyelid. When the device 100 is in the desired position, the user then uses his/her index finger, as shown in FIG. 27 to depress the activation switch 180. By pressing the activation switch 180 to the first position, the activation indicator 1310 is illuminated, indicating that the device 100 is ready for operation.

If the optical targeting mechanism 1540 is used, the user aims the device 100 generally toward the patient's eye and, using his/her forefinger, as shown in FIG. 27, depresses the activation switch 180 to the first position. The activation indicator 1310 is illuminated, indicating that the device 100 is ready for operation. Also, the light sources 1546, 14538 on the targeting mechanism 1540 are illuminated, projecting images onto the patient's eye. Preferably, the images are any of the images shown in FIGS. 17a-21c. The user can adjust the distance and aim of the device 100 relative to the patient's eye based on the images projected onto the patient's eye.

The remainder of the description of the operation of the device 100 is the same whether the device 100 is being used for self-administration of medication or whether the device 100 is being used by a professional to administer medication to a patient.

The user presses the activation switch 180 to the second position and then releases the activation switch 180, transmitting a signal to the system controller 190 to operate the prime mover 140. An electronic operational signal is transmitted through the power management circuit 194 and the VSD circuit 198 to the prime mover 140 which, in the case of the piezoelectric device described above, causes the piezoelectric device to vibrate, preferably at an ultrasonic frequency, along its longitudinal axis 148. The prime mover 140 is operated for a predetermined amount of time, preferably between approximately 0.5 and 2 seconds, as programmed into the system controller 190 prior to use. The prime mover 140 operates for the predetermined amount of time, regardless of how long the activation switch 180 is depressed, unless the activation switch 180 is depressed in excess of a predetermined period of time, such as 5 seconds, as will be described in more detail later herein.

The vibration of the prime mover 140 draws fluid 122 from the reservoir 120 and through the lumen 1410. The fluid 122 exits the distal end 144 of the prime mover 140 and passes through the openings 1520 in the mesh plate 156, where the fluid 122 is broken into micron-sized particles, which are directed toward the patient's eye. After the prime mover 140 has operated for the predetermined period of time, the system controller 190 ceases to transmit the operational signal and the prime mover 140 stops. At this time, the system controller 190 transmits a signal to the dose complete indicator 1920 to indicate to the user that the dosage is complete.

If the user is using the mechanical targeting means 1620, the user preferably removes the connected end 1624 from the spacer recess 137 and discards the elongated member 1622 to ensure that any bacteria from the patient's eye is not transmitted to the targeting means 1620 and then retransmitted to the next patient.

If the level of the fluid 122 in the reservoir 120 drops below a predetermined level, the low reservoir sensor 1250 transmits a signal to the system controller 190, which in turn transmits a signal to the low reservoir indicator 1914, informing the user that the reservoir 120 must be removed and a new reservoir must be inserted into the body 130.

If the low battery indicator 194 indicates that the power source 170 is at lower power, the user may insert the device 100 into the base 166 to charge the power source 170, or alternatively, replace the power source 170.

In the event that the user desires to change medication in the reservoir 120, it is recommended that the device 100 be "flushed" after removing the original medication but before using the new medication, so as not to contaminate the new medication with the old medication. In such an instance, the user inserts a reservoir containing a cleaning fluid, such as a saline solution into the body 130, and depresses the activation switch 180 in excess of a predetermined period of time, such as 5 seconds. The system controller 190 recognizes the extended depression of the activation switch 180 as the start of a cleaning cycle and operates the prime mover 140 for an extended period of time, such as for 30 seconds, or some other predetermined time, as desired. At the end of the cleaning cycle, the dose complete indicator 1920 may activate, alerting the user that the device 100 is clean, and that a new medication may now be used in the device 100.

While the embodiments of the present invention described above are preferably used to deliver medicament to a patient's eye, those skilled in the art will recognize that the embodiments of the present invention may be used with a respiratory medication instead of an ophthalmic medication, and that the invention may be used in the treatment of respiratory ailments instead of ophthalmic ailments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An ophthalmic fluid atomizer configured to deliver an ophthalmic fluid to an eye, the ophthalmic fluid atomizer comprising:
    a body having a proximal end and a distal end;
    a reservoir connected to the body, wherein the reservoir contains an ophthalmic fluid disposed therein;
    a discharge plate disposed at the distal end, wherein the discharge plate includes a plurality of openings extending therethrough;
    propulsion means for transmitting the ophthalmic fluid from the reservoir to the discharge plate, wherein transmission of the ophthalmic fluid across the discharge plate generates a plume of ophthalmic fluid along a direction directly toward the eye, wherein the plume of ophthalmic fluid travels, without being subject to a dynamic force generated by a mechanical device of the ophthalmic fluid atomizer that is physically separate from the propulsion means, from the discharge plate to the eye and at the eye has a momentum that has a magnitude that is insufficient to trigger at least one of an ocular blink reflex and a lacrimation reflex of the eye;
    a processor electronically connected to the propulsion means, wherein the processor controls operation of the propulsion means;
    an activation switch operatively coupled to the processor to activate the propulsion means; and
    an adjustable dosage adjuster, physically separate from the activation switch, operatively coupled to the processor and configured to adjust discharge duration of the ophthalmic fluid from the propulsion means.

2. The ophthalmic fluid atomizer according to claim 1, wherein the atomizer discharges the ophthalmic fluid having a velocity of between approximately 4 and 30 centimeters per second.

3. The ophthalmic fluid atomizer according to claim 1, wherein the atomizer operates for approximately 0.5 to 5 seconds upon activation of the activation switch.

4. The ophthalmic fluid atomizer according to claim 1, further comprising means for transmitting data between the processor and an external device.

5. The ophthalmic fluid atomizer according to claim 1, further comprising means for operating the atomizer for a period in excess of five seconds.

6. The ophthalmic fluid atomizer according to claim 1, further comprising a low level alert operatively connected to the processor, wherein the low level alert transmits a signal that the ophthalmic fluid is at a low level in the reservoir.

7. The ophthalmic fluid atomizer according to claim 1, further comprising means for adjusting operation of the propulsion means to adjust an amount of the ophthalmic fluid transmitted across the discharge plate.

8. The ophthalmic fluid atomizer according to claim 7, wherein the means for adjusting operation of the propulsion means are operatively connected to the processor.

9. The ophthalmic fluid atomizer according to claim 1, wherein the activation switch is operable among an off position, a first operating position, and a second operating position.

10. The ophthalmic fluid atomizer according to claim 9, wherein, upon engaging the activation switch in the second operating position, the processor transmits an operating signal to the propulsion means for no more than five seconds.

11. The ophthalmic fluid atomizer according to claim 9 wherein, upon engaging the activation switch in the first operating position, the system controller transmits a signal to a user that the device is ready for operation.

12. The ophthalmic fluid atomizer according to claim 9, wherein the first operating position is operatively disposed between the off position and the second position.

13. The ophthalmic fluid atomizer according to claim 9, further comprising an indicator signal operatively coupled to the activation switch and configured to operate when the activation switch is in the first position.

14. The ophthalmic fluid atomizer according to claim 9, wherein the activation switch is configured to operate the propulsion means when the activation switch is in the second position.

15. The ophthalmic fluid atomizer according to claim 9, wherein the activation switch is operatively coupled to the propulsion means and configured to operate the propulsion means for a predetermined period of time independent of a duration of the operation of the activation switch.

16. The ophthalmic fluid atomizer according to claim 1, further comprising a low level alert operatively connected to the processor, wherein the low level alert transmits a signal that the fluid is at a low level in the reservoir.

17. The ophthalmic fluid atomizer according to claim 1, further comprising a flow controller operatively coupled to the processor to adjust flow rate of the ophthalmic fluid from the propulsion means.

18. The ophthalmic fluid atomizer according to claim 17, wherein the flow controller is preprogrammed.

19. The ophthalmic fluid atomizer according to claim 1, wherein the propulsion means extends into the reservoir.

20. The ophthalmic fluid atomizer according to claim 1, wherein the ophthalmic fluid is selected from the group consisting of mydriatics/cycloplegics, anesthetics, flourescein, flourescein/anesthetic combinations, mydriatic reversal agents, ophthalmic decongestants, ophthalmic lubricants, and glaucoma medications.

21. The ophthalmic fluid atomizer according to claim 20, wherein the glaucoma medications are selected from the group consisting of prestaglandins, beta blockers, alpha adrenergic agents, carbonic anhydrase inhibitors, and miotics.

22. The ophthalmic fluid atomizer according to claim 1, wherein the plume of ophthalmic fluid has a volume that can entirely be retained by the eye.

23. The ophthalmic fluid atomizer according to claim 1, wherein the plume of ophthalmic fluid has a volume of greater than or equal to 1 micro liter and less than or equal to 5 micro liters.

24. The ophthalmic fluid atomizer according to claim 1, further comprising means for spacing the discharge plate a predetermined distance from an eye, wherein the means for spacing the discharge plate comprises at least one light projected toward the eye.

25. The ophthalmic fluid atomizer of claim 1, wherein the plume of ophthalmic fluid contains an amount of ophthalmic medicine and the momentum of the plume is such that substantially all of the amount of ophthalmic medicine is received and retained by the human eye.

26. An ophthalmic fluid atomizer configured to deliver an ophthalmic fluid to an eye the ophthalmic fluid atomizer comprising:
- a body having a proximal end and a distal end;
- a reservoir connected to the body, wherein the reservoir contains an ophthalmic fluid disposed therein;
- a discharge plate disposed at the distal end, wherein the discharge plate includes a plurality of openings extending therethrough;
- propulsion means for transmitting the ophthalmic fluid from the reservoir to the discharge plate, wherein transmission of the ophthalmic fluid through the plurality of openings atomizes the ophthalmic fluid and generates a plume of ophthalmic fluid along a direction directly toward the eye, wherein the plume of ophthalmic fluid travels, without being subject to a dynamic force generated by a mechanical device of the ophthalmic fluid atomizer that is physically separate from the propulsion means, from the discharge plate to the eye and at the eye has a momentum that has a magnitude that is insufficient to trigger at least one of an ocular blink reflex and a lacrimation reflex of the eye;
- a processor electronically connected to the propulsion means, wherein the processor controls operation of the propulsion means; and
- an activation switch operatively coupled to the processor and configured to operate the propulsion means for a predetermined period of time, said predetermined period of time having a duration which is independent of operation of the activation switch.

27. The ophthalmic fluid atomizer according to claim 26, wherein the ophthalmic fluid is selected from the group consisting of mydriatics/cycloplegics, anesthetics, flourescein, flourescein/anesthetic combinations, mydriatic reversal agents, ophthalmic decongestants, ophthalmic lubricants, and glaucoma medications.

28. The ophthalmic fluid atomizer according to claim 27, wherein the glaucoma medications are selected from the group consisting of prestaglandins, beta blockers, alpha adrenergic agents, carbonic anhydrase inhibitors, and miotics.

29. The ophthalmic fluid atomizer according to claim 26, wherein the plume of ophthalmic fluid has a volume that can entirely be retained by the eye.

30. The ophthalmic fluid atomizer according to claim 26, wherein the plume of ophthalmic fluid has a volume of greater than or equal to 1 micro liter and less than or equal to 5 micro liters.

31. The ophthalmic fluid atomizer of claim 26, wherein the mist contains an amount of ophthalmic medicine and the momentum of the mist is such that substantially all of the amount of ophthalmic medicine is received and retained by the human eye.

32. The ophthalmic fluid atomizer according to claim 26, wherein the atomizer discharges the ophthalmic fluid having a velocity of between approximately 4 and 30 centimeters per second.

33. The ophthalmic fluid atomizer according to claim 26, further comprising means for spacing the discharge plate a predetermined distance from an eye, wherein the means for spacing the discharge plate comprises at least one light projected toward the eye.

34. The ophthalmic fluid atomizer according to claim 26, wherein the reservoir is removable.

35. An ophthalmic fluid misting device adapted to deliver an ophthalmic fluid to an eye comprising:
a) a body having a proximal end and a distal end;
b) a prime mover coupled to the body;
c) a discharge plate coupled to the distal end of the body;
d) a targeting device mounted on the body for spacing the discharge plate a predetermined distance from the eye;
e) a prefilled medication reservoir releasably coupled to the proximal end of the body, the medication reservoir comprising:
  i) a vent having a vent covering comprising a liquid impermeable/gas permeable material,
  ii) a seal operable between a closed position prior to coupling the reservoir to the body and an open position when the reservoir is coupled to the body, and
  iii) a sterile ophthalmic fluid disposed within the reservoir;
f) a processor operatively coupled to the prime mover for regulating operation of the prime mover;
g) an activation switch operatively coupled to the processor such that a single operation of the activation switch activates the prime mover for a predetermined period of time; and
h) an adjustable dosage adjuster, physically separate from the activation switch, operatively coupled to the processor to operate the prime mover for the predetermined period of time regardless of a duration of the operation of the activation switch, wherein during the predetermined period of time the prime mover and the discharge plate have a structure that generates a plume of ophthalmic fluid in mist form along a direction directly toward the eye, wherein the plume of ophthalmic fluid travels, without being subject to a dynamic force generated by a mechanical device of the ophthalmic fluid misting device that is physically separate from the prime mover,—from the discharge plate to the eye and at the eye has a momentum that has a magnitude that is insufficient to trigger at least one of an ocular blink reflex and a lacrimation reflex of the eye.

36. The ophthalmic fluid misting device according to claim 35, wherein the discharge plate is releasably connected to the body.

37. The ophthalmic fluid misting device according to claim 35, wherein the plume of ophthalmic fluid has a volume that can entirely be retained by the eye.

38. The ophthalmic fluid misting device according to claim 35, wherein the plume of ophthalmic fluid has a volume of greater than or equal to 1 micro liter and less than or equal to 5 micro liters.

39. The ophthalmic fluid misting device according to claim 35, further comprising means for spacing the discharge plate a predetermined distance from an eye, wherein the means for spacing the discharge plate comprises at least one light projected toward the eye.

40. The ophthalmic fluid misting device of claim 35, wherein the plume of ophthalmic fluid contains an amount of ophthalmic medicine and the momentum of the plume is such that substantially all of the amount of ophthalmic medicine is received and retained by the human eye.

41. The ophthalmic fluid misting device according to claim 35, wherein the ophthalmic fluid is selected from the group consisting of mydriatics/cycloplegics, anesthetics, flourescein, flourescein/anesthetic combinations, mydriatic reversal agents, ophthalmic decongestants, ophthalmic lubricants, and glaucoma medications.

42. The ophthalmic fluid misting device according to claim 41, wherein the glaucoma medications are selected from the group consisting of prestaglandins, beta blockers, alpha adrenergic agents, carbonic anhydrase inhibitors, and miotics.

43. An ophthalmic fluid misting device adapted to deliver an ophthalmic fluid to an eye comprising:

a) a body and a reservoir connected to the body, wherein the reservoir contains an ophthalmic fluid disposed therein;
b) a mover of the ophthalmic fluid coupled to the body;
c) a processor operatively coupled to the mover for regulating operation of the mover;
d) an activation switch operatively coupled to the processor such that a single operation of the activation switch activates the mover for a predetermined period of time;
e) an adjustable dosage adjuster, physically separate from the activation switch, operatively coupled to the processor to operate the mover for the predetermined period of time regardless of a duration of the operation of the activation switch, wherein during the predetermined period of time the mover has a structure that generates a plume of ophthalmic fluid in mist form along a direction directly toward the eye, wherein the plume of ophthalmic fluid travels to the eye and at the eye has a momentum that has a magnitude that is insufficient to trigger to at least one of an ocular blink reflex and a lacrimation reflex of the eye, and
f) an output device electronically coupled to the processor, wherein the output device is adapted to receive information from the processor.

44. The ophthalmic fluid misting device according to claim 43, wherein the plume of ophthalmic fluid has a volume that can entirely be retained by the eye.

45. The ophthalmic fluid misting device according to claim 43, wherein the plume of ophthalmic fluid has a volume of greater than or equal to 1 micro liter and less than or equal to 5 micro liters.

46. The ophthalmic fluid misting device according to claim 43, further comprising:
a discharge plate at a distal end of the body; and
means for spacing the discharge plate a predetermined distance from an eye, wherein the means for spacing the discharge plate comprises at least one light projected toward the eye.

47. The ophthalmic fluid misting device of claim 43, wherein the plume of ophthalmic fluid contains an amount of ophthalmic medicine and the momentum of the plume is such that substantially all of the amount of ophthalmic medicine is received and retained by the human eye.

48. The ophthalmic fluid misting device according to claim 43, wherein the ophthalmic fluid is selected from the group consisting of mydriatics/cycloplegics, anesthetics, flourescein, flourescein/anesthetic combinations, mydriatic reversal agents, ophthalmic decongestants, ophthalmic lubricants, and glaucoma medications.

49. The ophthalmic fluid misting device according to claim 48, wherein the glaucoma medications are selected from the group consisting of prestaglandins, beta blockers, alpha adrenergic agents, carbonic anhydrase inhibitors, and miotics.

50. An ophthalmic fluid atomizer comprising:
a body having a proximal end and a distal end;
a reservoir connected to the body, wherein the reservoir contains an ophthalmic fluid disposed therein;
a discharge plate disposed at the distal end, wherein the discharge plate includes a plurality of openings extending therethrough;
an ultrasonic generator located in the body for transmitting the ophthalmic fluid from the reservoir to the discharge plate, wherein the discharge plate and the ultrasonic generator have a structure for generating a plume of ophthalmic fluid along a direction directly toward the eye, wherein the plume of ophthalmic fluid travels, without being subject to a dynamic force generated by a mechanical device of the ophthalmic fluid atomizer that is physically separate from the ultrasonic generator, from the discharge plate to the eye and at the eye has a momentum that has a magnitude that is insufficient to trigger at least one of an ocular blink reflex and a lacrimation reflex of the eye;
the ultrasonic generator disposed between the proximal and distal ends and in fluid communication with the reservoir and the discharge plate;
a processor electronically connected to the ultrasonic generator, wherein the processor controls operation of the ultrasonic generator;
an activation switch operatively coupled to the processor to activate the ultrasonic generator;
an adjustable dosage adjuster, physically separate from the activation switch, operatively coupled to the processor, and configured to adjust discharge duration of the ophthalmic fluid from the device; and
a flow controller operatively coupled to the processor to adjust flow rate of the ophthalmic fluid from the ultrasonic generator.

51. The ophthalmic fluid atomizer according to claim 50, wherein the plume of ophthalmic fluid has a volume that can entirely be retained by the eye.

52. The ophthalmic fluid atomizer according to claim 50, wherein the plume of ophthalmic fluid has a volume of greater than or equal to 1 micro liter and less than or equal to 5 micro liters.

53. The ophthalmic fluid atomizer according to claim 50, further comprising means for spacing the discharge plate a predetermined distance from an eye, wherein the means for spacing the discharge plate comprises at least one light projected toward the eye.

54. The ophthalmic fluid atomizer of claim 50, wherein the plume of ophthalmic fluid contains an amount of ophthalmic medicine and the momentum of the plume is such that substantially all of the amount of ophthalmic medicine is received and retained by the human eye.

55. The ophthalmic fluid atomizer according to claim 50, wherein the ophthalmic fluid is selected from the group consisting of mydriatics/cycloplegics, anesthetics, flourescein, flourescein/anesthetic combinations, mydriatic reversal agents, ophthalmic decongestants, ophthalmic lubricants, and glaucoma medications.

56. The ophthalmic fluid atomizer according to claim 55, wherein the glaucoma medications are selected from the group consisting of prestaglandins, beta blockers, alpha adrenergic agents, carbonic anhydrase inhibitors, and miotics.

57. An ophthalmic fluid atomizer comprising:
a body having a proximal end and a distal end;
a reservoir engaging surface disposed at the distal end for receiving a reservoir containing an ophthalmic fluid disposed therein;
a discharge plate disposed at the distal end, wherein the discharge plate includes a plurality of openings extending therethrough;
an ultrasonic generator located in the body for transmitting the ophthalmic fluid from the reservoir to the discharge plate, wherein the discharge plate and the ultrasonic generator have a structure for generating a plume of ophthalmic fluid along a direction directly toward the eye, wherein the plume of ophthalmic fluid travels, without being subject to a dynamic force generated by a mechanical device of the ophthalmic fluid atomizer that is physically separate from the ultrasonic generator, from the discharge plate to the eye and at the eye has a momentum that has a magnitude that is insufficient to trigger at least one of an ocular blink reflex and a lacrimation reflex of the eye;

the ultrasonic generator disposed between the proximal and distal ends and in fluid communication with the discharge plate;

a processor electronically connected to the ultrasonic generator, wherein the processor controls operation of the ultrasonic generator;

an activation switch operatively coupled to the processor to activate the ultrasonic generator; and an adjustable dosage adjuster, physically separate from the activation switch, operatively coupled to the processor, and configured to adjust discharge duration of the ophthalmic fluid from the device.

58. The ophthalmic fluid atomizer according to claim 57, wherein the plume of ophthalmic fluid has a volume that can entirely be retained by the eye.

59. The ophthalmic fluid atomizer according to claim 57, wherein the plume of ophthalmic fluid has a volume of greater than or equal to 1 micro liter and less than or equal to 5 micro liters.

60. The ophthalmic fluid atomizer according to claim 57, further comprising means for spacing the discharge plate a predetermined distance from an eye, wherein the means for spacing the discharge plate comprises at least one light projected toward the eye.

61. The ophthalmic fluid atomizer of claim 57, wherein the plume of ophthalmic fluid contains an amount of ophthalmic medicine and the momentum of the plume is such that substantially all of the amount of ophthalmic medicine is received and retained by the human eye.

62. The ophthalmic fluid atomizer according to claim 57, wherein the ophthalmic fluid is selected from the group consisting of mydriatics/cycloplegics, anesthetics, flourescein, flourescein/anesthetic combinations, mydriatic reversal agents, ophthalmic decongestants, ophthalmic lubricants, and glaucoma medications.

63. The ophthalmic fluid atomizer according to claim 62, wherein the glaucoma medications are selected from the group consisting of prestaglandins, beta blockers, alpha adrenergic agents, carbonic anhydrase inhibitors, and miotics.

64. An ophthalmic fluid atomizer comprising:

a body having a proximal end and a distal end;

a reservoir connected to the body, wherein the reservoir contains an ophthalmic fluid disposed therein;

a discharge plate disposed at the distal end, wherein the discharge plate includes a plurality of openings extending therethrough;

propulsion means for transmitting the ophthalmic fluid from the reservoir to the discharge plate, wherein transmission of the ophthalmic fluid across the discharge plate generates a plume of ophthalmic fluid along a direction directly toward the eye, wherein the plume of ophthalmic fluid travels, without being subject to a dynamic force generated by a mechanical device of the ophthalmic fluid atomizer that is physically separate from the propulsion means, unassisted from the discharge plate to the eye and at the eye has a momentum that has a magnitude that is insufficient to trigger at least one of an ocular blink reflex and a lacrimation reflex of the eye;

a processor electronically connected to the propulsion means, wherein the processor controls operation of the propulsion means;

an activation switch operatively coupled to the processor to activate the propulsion means; and means for adjusting the flow rate of ophthalmic fluid from the propulsion means.

65. The ophthalmic fluid atomizer according to claim 64, wherein the plume of ophthalmic fluid has a volume that can entirely be retained by the eye.

66. The ophthalmic fluid atomizer according to claim 64, wherein the plume of ophthalmic fluid has a volume of greater than or equal to 1 micro liter and less than or equal to 5 micro liters.

67. The ophthalmic fluid atomizer according to claim 64, further comprising means for spacing the discharge plate a predetermined distance from an eye, wherein the means for spacing the discharge plate comprises at least one light projected toward the eye.

68. The ophthalmic fluid atomizer of claim 64, wherein the plume of ophthalmic fluid contains an amount of ophthalmic medicine and the momentum of the plume is such that substantially all of the amount of ophthalmic medicine is received and retained by the human eye.

69. The ophthalmic fluid atomizer according to claim 64, wherein the ophthalmic fluid is selected from the group consisting of mydriatics/cycloplegics, anesthetics, flourescein, flourescein/anesthetic combinations, mydriatic reversal agents, ophthalmic decongestants, ophthalmic lubricants, and glaucoma medications.

70. The ophthalmic fluid atomizer according to claim 69, wherein the glaucoma medications are selected from the group consisting of prestaglandins, beta blockers, alpha adrenergic agents, carbonic anhydrase inhibitors, and miotics.

* * * * *